United States Patent [19]
Gregoriadis

[11] Patent Number: 5,846,951
[45] Date of Patent: Dec. 8, 1998

[54] PHARMACEUTICAL COMPOSITIONS

[75] Inventor: Gregory Gregoriadis, Middlesex, United Kingdom

[73] Assignee: The School of Pharmacy, University of London, United Kingdom

[21] Appl. No.: 431,474

[22] Filed: May 1, 1995

Related U.S. Application Data

[62] Division of Ser. No. 157,128, Dec. 6, 1993.

[30] Foreign Application Priority Data

Jun. 6, 1991 [GB] United Kingdom ............... 9112212

[51] Int. Cl.$^6$ .................... A61K 31/715; A61K 9/62; A61K 9/127
[52] U.S. Cl. ................. 514/54; 514/42; 424/450; 424/461
[58] Field of Search .................. 514/42, 54, 60; 424/450, 461; 536/17.2, 18.7, 123, 123.1

[56] References Cited

U.S. PATENT DOCUMENTS

| | | | |
|---|---|---|---|
| 4,501,728 | 2/1985 | Geho et al. | 424/38 |
| 4,837,028 | 6/1989 | Allen | 424/450 |
| 5,000,959 | 3/1991 | Iga | 424/450 |

FOREIGN PATENT DOCUMENTS

| | | |
|---|---|---|
| 0351808 | 1/1990 | European Pat. Off. . |
| 0349127 | 3/1990 | European Pat. Off. . |
| 0454898 | 6/1991 | European Pat. Off. . |
| 63241001 | 10/1988 | Japan . |
| 63313724 | 12/1988 | Japan . |
| 05222085 | 8/1993 | Japan . |
| 06080686 | 3/1994 | Japan . |
| 8604065 | 7/1986 | WIPO . |
| 9113079 | 9/1991 | WIPO . |

OTHER PUBLICATIONS

Biochemica et Biophysica Acta, vol. 986, 1989, Amsterdam, NL, pp. 106–114, Abstract Pinnaduwge et al 'The Role of Protein–Linked Oligosaccharide in the Bilayer Staliziation Activity of Glycophorin A For Dioleoylphosphatidylethanolamine Liposomes'.

Biochemica et Biophysica Acta, vol. 1023, 1990, Amsterdam, NL, pp. 357–364, Abstract Decher et al 'Giant Liposomes as Model Membranes for Immunological Studies: Spontaneous Insertion of Purified K1–Antigen (Poly–Alpha–2,8–Neuac) of Escherichia Coli'.

Chemical Abstracts, vol. 107, 1987, Columbus, Ohio, US; Abstract No. 28327p, Sunamoto et al 'Utilization of Functionalized Liposomes as Improved Artificial Cells' p. 319; col. 2; see abstract & Kenkyu Hokoku–Asahi Garasu Kogyo Gijutsu Shoreikai, vol. 48, 1986, pp. 231–239, Sunamoto et al.

Journal of Immunology, vol. 127, No. 3, Sep. 1981, Baltimore, USA, pp. 1011–1018, Jennings et al 'Immunochemistry of Groups A, B and C Meningococcal Polysaccharide–Tetanus Toxoid Conjugates' cited in the application — see the whole document.

Yamauchi et al., *Int. J. Pharm.*, vol. 113(3): 141–148, (1995). Abstract only.

Sunamoto et al., *Chem. Lett.*, vol. 10 : 1781–1784, (1988). Abstract only.

Carbohydr. Res. vol 156 (1986) Lifely et al. (abstract only).

*Primary Examiner*—John Kight
*Assistant Examiner*—Howard C. Lee
*Attorney, Agent, or Firm*—Ostrolenk, Faber, Gerb & Soffen, LLP

[57] ABSTRACT

Polysaccharides comprising at least 5 sialic acid residues per molecule are used to increase the circulation time of an active ingredient, for instance by decreasing the immunogenicity and/or increasing the stability in vivo of pharmaceutically active compounds. The pharmaceutically active compound may be a foreign protein which is covalently bound to the polysaccharide. Alternatively, the active compound may be associated with a drug delivery system (DDS), for instance a macro-molecular DDS or a particulate DDS, such as liposomes. The polysaccharide is usually a bacterial polysaccharide, e.g., a glycolipid or a derivative thereof, for instance polysaccharide B or *E. Coli* K1, *N. meningitidis*, *Moraxella liquifaciens* or *Pasteurella aeroginosis*, or K92 of *E. Coli* K92 strain.

37 Claims, 12 Drawing Sheets

Scheme 1

Coupling of 1-bromooctadecane with Colominic Acid a) Preparation of Colominic Acid Crown Ether
  b) Coupling of the Colominic Acid Crown Ether with 1-bromooctadecane.

Fig. 12 a

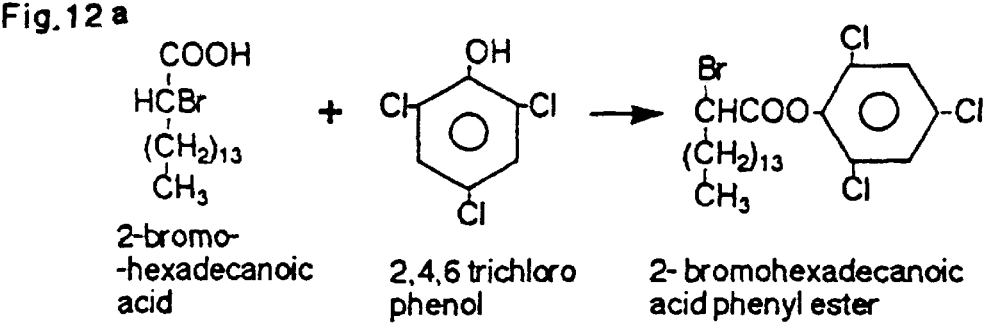

2-bromo-
-hexadecanoic
acid 2,4,6 trichloro
phenol 2-bromohexadecanoic
acid phenyl ester

Fig. 12 b

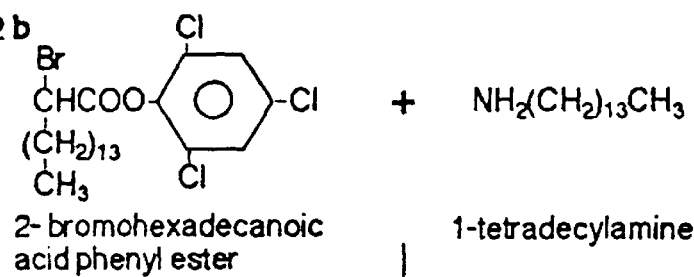

2-bromohexadecanoic
acid phenyl ester 1-tetradecylamine

Fig. 12 c

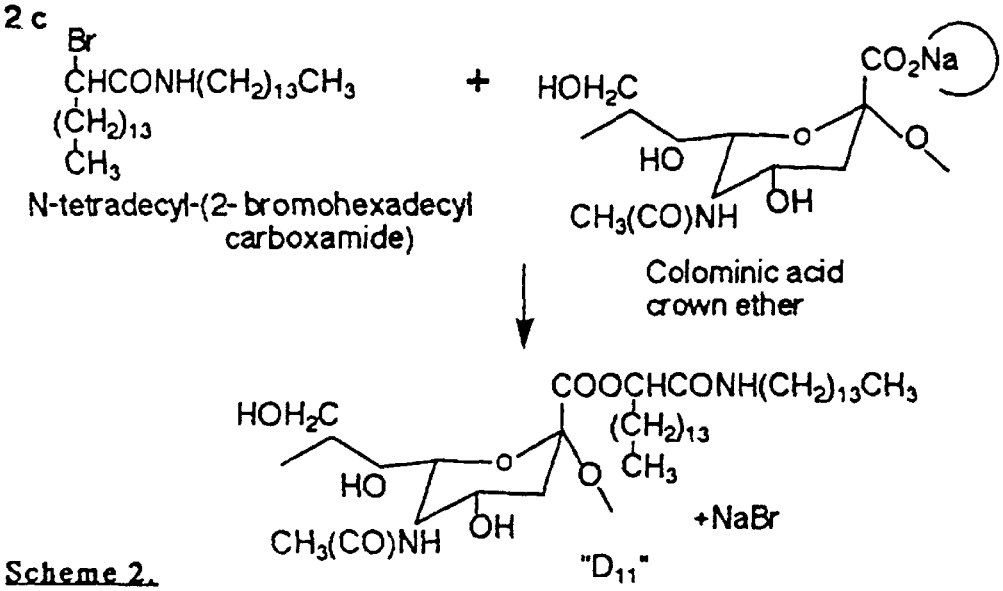

N-tetradecyl-(2-bromohexadecyl
carboxamide)

Colominic acid
crown ether

"D₁₁"

Scheme 2.

Coupling of the N-tetradecyl-(2-bromohexadecylcarboxamide) with colominic acid crown ether.

a) Preparation of 2-bromohexadecanoic acid phenyl ester.
b) Coupling of the 2-bromohexadecanoic acid phenyl ester with 1-tetradecylamine.
c) Coupling of N-tetradecyl(2-bromohexadecylcarboxamide) with colominic acid crown ether.

PHARMACEUTICAL COMPOSITIONS

This is a Continuation of application Ser. No. 08/157,128 filed on Dec. 6, 1993.

The present invention relates to the use of a polysaccharide or polysaccharide derivative in association with a pharmaceutically active compound to extend the residence time of the active compound in the circulation of a patient or to deliver the compound to a specific target within the body of a patient.

There exists a great variety of pharmacologically active agents for which there is a need either to maintain an elevated concentration in the circulating blood or to deliver them directly to the site of action. Such agents include conventional drugs, peptides and proteins and oligonucleotides used in cancer and antimicrobial therapy and in enzyme or hormone replacement therapy and in immunology. In many instances, agents exhibit a short half-life in the circulation being rapidly excreted through the kidneys or taken up by the reticuloendothelial system (RES) and other tissues. To compensate for such premature drug loss, larger doses are required so that sufficient amounts of drug can concentrate in areas in need of treatment. However this is not only costly, it can also lead to toxicity and an immune response to the "foreign protein". For instance, cytokines such as interferon (IFN-$\gamma$) and interleukin-2 (IL-2) would be more effective, less toxic and also used in smaller quantities, if their presence in the circulation could be extended.

Recent advances in recombinant DNA technology have made available a wide range of biologically active proteins. Although in some instances molecular remodelling for instance by ligated gene fusion or by site directed mutagenesis has endowed such proteins with properties compatible with optimal activity, it is generally the case that effective use of these products can only be achieved through delivery systems. It would be desirable to prevent premature loss of drug without, or in conjunction with, targeted delivery systems.

A drug delivery system (DDS) is any molecular or particulate entity which can control to our advantage the fate and effect of drugs associated with the entity. DDS can be separated into two general types. The first type comprises macromolecules (MDDS), for instance antibodies, neoglycoproteins as well as synthetic polymers, such as poly (hydroxypropylmethacrylamide), polylysine and polymerised alkyl cyanoacrylates. The association of drugs with various types of macromolecular carriers, including monoclonal antibodies to target the drug to the desired sites is described for instance by Gregoriadis in Nature 265, 407–411 (1977).

The second type is particulate DDS (PDDS), which comprises for instance nanospheres or microspheres, which comprise biodegradable materials such as albumin or semi-biodegradable materials such as dextran and alkylcyanoacrylate polymers, or vesicles formed of nonionic surfactants or liposomes.

Drugs can either be covalently linked to, or passively entrapped into, the DDS. For instance, PDDS comprising surfactant vesicles or liposomes may entrap hydrophilic or hydrophobic pharmaceutically active compounds by being formed of an appropriate combination of layers of surfactant or lipid molecules. Pharmaceutically active compounds are usually covalently linked to MDDS, by a bond which may or may not be lysed in the body, for instance before or after the active compound performs its function. Liposomes are discussed by Gregoriadis in NIPS, 4, 146–151 (1989) and in "Liposomes as Drug Carriers: Recent Trends and Progress" Ed Gregoriadis (1988) Wiley.

Many of the MDDS have an intrinsic (eg antibodies) or acquired (eg neoglycoproteins) ability to be recognised by target cells or tissues through receptors on the latter's surface. Typically, such DDS are taken up specifically by the target upon injection. Specific uptake is, however, limited with the bulk of the DDS being taken up by other, irrelevant (to therapy) tissues. The reason for this is that antibodies and other DDS proteins (regardless of their specificity for the target) must be, like other proteins, catabolised at the end of their biological life.

Protein molecules do not have a fixed life span and they die randomly. Thus, from the moment of injection protein molecules (together with their drug load) begin to be catabolised at a linear rate with only some of the molecules being able to come into contact with and taken up by, the target.

DDS such as mouse antibodies are foreign when injected in another species. The host species develops antibodies to deal with the foreign protein on subsequent injection. Such proteins are removed from the circulation after the first injection by mechanisms which are poorly understood. DDS such as man-made polymers are recognised by opsonins and removed by the reticulo-endothelial system (RES), mostly liver and spleen macrophages. In each case, the sequence of events includes and is usually initiated by recognition of and binding to the DDS component by host organism proteins. Disruption of the recognition and or binding steps interferes with the catabolism of the component molecules.

Synthetic polymers used in the macromolecular type MDDS are for instance poly (hydroxypropylmethacrylamide) polylysine and polymerised alkyl cyanoacrylates. These may be catabolised in the RES system or other tissues by appropriate lysosomal enzymes. It would be desirable to reduce the rate of catabolism of such biodegradable macromolecular type DDS by some means, for instance by reducing uptake of the DDS by the RES or other tissues, or by reducing degradation by lysosomal enzymes once taken up by the RES.

Particulate DDS (PDDS) are, as a rule, removed from the circulation by the RES. Because of their propensity for the RES, PDDS are often used for the delivery of drugs to these tissues. It is often desirable, however, that PDDS are directed to tissues other than those of the RES. To achieve this goal, one must block or delay RES interception of PDDS.

This has been accomplished to some extent by coating PDDS with hydrophilic macromolecules such as polyethyleneglycol (PEG) or of ethylene oxide and propylene oxide, including such blocks formed of ethylene diamine, available under the trade names Pluronic, Tetronic, Poloxamer and Poloxamine. These polymers are man made. Their use is described in by Illum in GB-A-2185397, by Illum and Davis in FEBS Letts. (1984) 167, 79–82, by Illum et al in Life Sciences (1987) 40, 367–374, by Hunter et al Scand. J. Immunol. 23, 287 (1986), by Senior et al in Biochem. Biophys. Acta (1991) 1062, 77–82 and in WO-A-9004384. PEG and block copolymers of ethylene oxide are highly hydrophilic, a property which is responsible for their ability to prevent or delay (a) recognition of PDDS (to which such polymers are attached) by tissues which take them up prematurely; (b) loss of drugs, peptides and proteins (to which such polymers are attached) through premature excretion or uptake by irrelevant tissues.

Abuchowski et al in J. Biol. Chem. (1977) 252, 3282–86 disclose the covalent attachment of PEG of two molecular weights (1900 and 5000) to catalase, which reduced the immunogenicity of the protein and increased its half life in the circulation of mice. Abuchowski suggests the process would allow the use of enzyme therapy for instance to alter blood metabolites or to treat storage diseases. However it would be desirable to increase the half life of proteins (and peptides etc) even further than PEG would appear to be capable.

Abuchowski et al also disclose that they rejected the idea of using dextran (a polysaccharide) in place of PEG since dextran is known to be immunogenic in humans. In GB-A-2185397 it is suggested that polysaccharides, xanthan and hyaluronic acid could be used in place of ethylene oxide-propylene oxide block copolymers to prevent uptake by the liver of colloidal particles. The presence of carboxyl groups in xanthan gum is said to be of benefit for the desired effect. No polysaccharides are actually tested nor is any information given as to how polysaccharides might be linked to the colloidal particle surface.

Senior et al (op. cit.) and WO-A-9004384 describe the coating of liposomes by polyethylene glycol (PEG) by covalent coupling of monomethoxy PEG to phospholipid. The coating resulted in the clearance time of liposomes from the blood being increased by up to 30% and in the liposomes adsorbing plasma components more slowly. Both factors were believed to result from the surface of the vesicles having been made more hydrophilic by the PEG.

In FEBS Letts. (1987) 283, 42–46, Allen & Chonn describe the incorporation of gangliosides and their asialyl derivatives into liposomes. Gangliosides are glycosphingolipids comprising 2 fatty acid chains (mainly stearic acid) sphingosine and an oligosaccharide component comprising 5 units including galactose and one sialic acid unit. The incorporation of ganglioside increased the circulation time of liposomes and caused an increase in the ratio of liposome found in the blood compared to the liver, indicating that RES uptake of the liposomes is reduced. The effect is less pronounced for asialylganglioside which is interpreted by the authors as indicating that the sialic acid and in particular its negative change on the liposome surface is important for the effect to be imparted.

In "Medical Application of Liposomes" (ed. K. Yogi) 1986 in the chapter entitled "Liposomes in Chemotherapy and Immunotherapy" p121–129, Sunamoto describes the coating of liposomes with various polysaccharides, including dextran, pullulan, amylopectin, amylose, and mannan in order to target the liposomes to specific tissues and cell, especially the lung. The data shows that encapsulation of drug in the polysaccharide-coated liposomes increase the circulation time of the drug (inulin) in the blood stream and in tissue when compared with free inulin. There is no data to compare stability and clearance of drug in coated and uncoated liposomes in the bloodstream; nor is the leakage of drug from liposomes and these facts cast doubt on the validity of the conclusions regarding the effect of polysaccharide coating; however, it might be expected from this document that the targetting of the liposomes by the polysaccharide coating to the lung or other tissues would reduce the circulation time of the liposomes. Other workers have described the use of glycoproteins and glycolipids for targetting liposomes, see for instance Gregoriadis 1989, 1988 and 1987 op. cit.

Jennings and Lugowski in J. Immunology (1981) 127, 1011–1018 describe the conjugation of meningococcal groups A, B and C polysaccharides to tetanus toxoid in order to increase the immunogenicity of the polysaccharide in an attempt to produce a vaccine for Neisseria meningitidis. The immunogenicity of Group B polysaccharide was not significantly increased, but the conjugate still elicited antibodies to the tetanus toxoid.

According to the present invention, there is provided the new use of a polysaccharide compound, the polysaccharide component of which contains more than 5 sialic acid units per molecule, in a process of manufacturing a pharmaceutical composition comprising an active ingredient, in which the polysaccharide is present in the composition in an amount sufficient to prolong the availability of the active ingredient in the circulation of a patient, to reduce the immunogenicity of the active ingredient and/or to increase the stability of the active ingredient in vivo.

In the invention there is also provided a new pharmaceutical composition comprising an active ingredient associated with a polysaccharide compound, the polysaccharide component of which contains more than 5 sialic acid units per molecule, in an amount sufficient to extend the availability of the active ingredient in the circulation of a patient to reduce the immunogenicity of the active ingredient and/or to increase the stability of the active ingredient in vivo.

In a further aspect of the invention, there is provided the new use of a polysaccharide compound, the polysaccharide component of which contains more than 5 sialic acid units per molecule, to prolong the availability of an active pharmaceutical ingredient in the circulation of a patient to reduce the immunogenicity of the active ingredient and/or to increase the stability of the active ingredient in vivo.

In the invention, the prolongation of the availability of the active ingredient in the circulation of a patient may be achieved either by preventing or delaying recognition of the pharmaceutically active ingredient or complex containing it by tissues which would otherwise take up the drug or drug complex, or by preventing or delaying loss of the pharmaceutical ingredient by premature excretion or uptake by therapeutically irrelevant tissues by means other than specific recognition. These effects also increase the stability of the active ingredient. The polysaccharide compound additionally or alternatively suppresses the immune response that would otherwise be illicited by the pharmaceutically active ingredient or complex containing it, by interfering with the initial recognition stages in the immune response. The invention is of primary use for pharmaceutical compositions for parenteral administration.

In the invention, the polysaccharide compound may be a naturally occurring polysaccharide, a derivative of a naturally occurring polysaccharide, for instance a polysaccharide which has been derivatised by reaction of one or more active groups on the saccharide residues, or which has been covalently linked to a derivatising group by either end of the polysaccharide chain or by an active group midway along the chain, or may be a naturally occurring polysaccharide derivative, for instance comprising attached phospholipids or proteins, or derivatives of naturally occurring polysaccharide derivatives, for instance chemically derivatised compounds, such as hydrolysed or otherwise chemically reacted derivatives. The polysaccharide portion of the compound has more than 5, preferably at least 10, and more preferably at least 20 or 50 sialic acid residues in the polymer chain. Readily available polysaccharide compounds may have up to 500 saccharide residues in total, but usually have fewer than 300 residues in the polymer chain. Preferably most or all the saccharide residues in the compound are sialic acid residues.

The polysialic acid portion at least of the polysaccharide compound, and preferably the entire compound, is highly hydrophilic. It is believed that high hydrophilicity reduces the likelihood of the polysaccharide compound being recognised or taken up by tissues and being catabolised. The hydrophilicity of the polysaccharide is conferred primarily by the pendant carboxyl groups of the sialic acid units as well as the hydroxyl groups. Other groups including groups on other saccharide units such as amine, hydroxyl or sulphate groups, or combinations of those groups may be present on the saccharide unit. Those groups may be present in the native polysaccharide compound or (less preferably) may be introduced by chemical reaction of native groups present. Preferably the polysaccharide is negatively charged in conditions found in the circulation i.e. when injected. The polysaccharide may comprise units of several different saccharides.

Polysaccharide compounds which are of particular use in the invention are polysaccharide compounds produced by bacteria. The natural compounds are often glycolipids, that is a compound comprising a polysaccharide component linked via phosphate ester linkages to phospholipids. Such glycolipids may be used in their native form in the invention or derivatives in which the fatty acid chains have been hydrolysed off the polysaccharide may be preferable in some instances.

Because sialic acid polysaccharides can be T-cell independent antigens, they (on injection) activate B cells directly to produce mainly IgM antibodies. These antibodies persist only for a few days and thus, polysaccharides are poor immunogens. This is an advantage in terms of using them in the present invention.

It is preferred for the polysaccharide compound to be substantially free of terminal galactose units since these may be recognised by galactose receptors on hepatocytes and Kuppfer cells and may therefore be cleared from circulation even faster.

Sialic acids (also known as nonulosonic acids) are members of a family of amino containing sugars containing 9 or more carbon atoms. The most important of the sialic acids is N-acetylneuraminic acid (also known as 5-(acetylamino)-3, 5-dideoxy-D-glycero-D-galacto-nonulosonic, lactaminic acid and O-sialic acid) which has the formula:

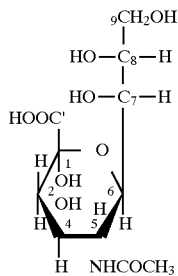

Polysialic acids may be linked 2→8 and/or 2→9, usually in the α-configuration.

Polysialic acids are generally found to be non-toxic and substantially non-immunogenic. Furthermore the biodegration units, sialic acid, is not known to be toxic and, indeed sialic acids are widely found in animal cells, including blood cells.

Polysaccharide compounds containing many sialic acid units are polysaccharides produced by *E-coli, Moraxella nonliquifaciens, Pasteurella aeroginosis* and *Neisseria meningitidis* or derivatives thereof. For instance, colominic acid derived (by hydrolysis to shorten the chain lengths) from *E. Coli* K1 comprises 2→8 αlinked sialic acid units and has an average chain length of about 16 units. Polysaccharide from *E. Coli* K92 stain comprises alternating 2→8 and 2→9 linked sialic acid units and has an average chain length of about 78 units. Polysaccharide C of *N. meningitidis* group C has 2→9 linked sialic acid units and has an average chain length of about 316 units. The deacetylated version of the last mentioned compound has an average chain length of about 172 units.

One group of polysaccharide compounds which has been found to be of particular utility in the invention is group B polysaccharides. These compounds are produced by *Neisseria meningitidis, Moraxella nonliquifaciens, Pasteurella aeroginosis* A2 and *E. coli* K1. These compounds comprise a polysaccharide component comprising sialic acid residues and a phospholipid component. The sialic acid residues are linked (2→8)-α, the naturally occurring polymer consisting of about 200 residues. The glycolipid appears to have a covalently attached phospholipid at the reducing end of the polysaccharide component.

It is preferable for the bacteria from which the polysaccharide compound is derived to be non-pathogenic for convenience during production. It is particularly suitable therefore for the polysaccharide to be derived from a non-pathogenic strain of *E. Coli* such as *E. Coli* K92. *E. Coli* K92 isolates are well-known and any such type of any such strain can be used as a source of suitable poly-saccharide.

A polysaccharide compound which is a glycolipid may be used either in the form of the naturally occurring glycolipid, or a derivative may be used. A particularly suitable derivative is one in which the fatty acid chains have been hydrolysed off the glycerophosphate group, to leave the polysialic acid glycerophosphate ester. The hydrolysis is usually by treatment with mild alkali. This treatment prevents the glycolipid molecules aggregating, which otherwise takes place in an aqueous medium by the hydrophobic interactions between the fatty acid chains of molecules. The deaggregation of *N. meningitidis* polysaccharide B is described by Lifely et al in "Gonococci and Meningococci" (1988) by Poolman et al (Eds) pp 147–152.

The native polysaccharides can be hydrolysed to form shorter chain lengths, for instance as described by Lifely et al in Carbohydrate Res (1986) 156, p123. The conditions in the hydrolysis reaction (for instance of time and temperature) can be selected so as to achieve a chosen average molecular weight of product.

The above mentioned polysaccharides may further be derivatised by N-deacetylating some or all of the 5-N-acetyl groups of the sialic acid units. The resultant 5-amine groups may be further derivatised, for instance by partial N-reacetylation, N-acylation by acids other than acetic acid, including amino acids or peptides or fatty acids.

Another way of derivatisation of the polysaccharides is by oxidation with sodium periodate which forms an aldehyde group at the non-reducing end of polysialic acid chain. A Schiff base reaction can then occur with an amino group of a drug (eg a protein side chain or end group).

It has been found that when these sialic acid-containing polysaccharide compounds are administered into the bloodstream of patients, a proportion is rapidly taken up from the bloodstream and the rest is eliminated, usually at steady rate. The half-life of the compound following the initial rapid take up step is a good indicator of the suitability of the polysaccharide compound in the invention for prolonging circulation times and/or stability of an active ingredient and/or reduce its immunogenecity, compounds with long half-lives being particularly suitable. Also the proportion of the compounds which is eliminated in the first rapid step is an indicator of the potential utility, useful compounds having none or only a small proportion of the compound removed from the circulation in the first step.

It is preferable for the polysaccharide compound used in the invention to be one of which less than about 50%, preferably less than about 25%, more preferably less than about 20%, is removed from the circulation following intravenous administration, for instance within a period of about 5 minutes from injection. A suitable polysaccharide compound, preferably has a half-life (in the animal being treated with the composition) following the rapid removal stage of at least 10 hours, preferably at least 20 hours, for instance 30 hours or more, for optimal effect. It is found that there is a correlation between the number of sialic acid units in the polysaccharide and the immediate removal and half life of the compound, such that compounds having more than about 20, more preferably more than 50 and more preferably more than 100, units on average have particularly good properties. Preferably therefore maximum chain length polysialic acid compounds are used, although for some uses it may be advantageous for the natural polysaccharide compound to be hydrolysed to shorter chain lengths, for instance to coat liposomes or conjugate with proteins.

In the inventions, the pharmaceutically active compound may be directly covalently linked to the polysaccharide compound. The active compound may be linked in stoichiometric amounts with the polysaccharide compound, that is one molecule of active ingredient may be linked to one molecule of polysaccharide compound. Alternatively, it may be convenient for two or more molecules of active ingredient to be covalently linked to one molecule of polysaccharide compound, or for two or more molecules of polysaccharide compound to be linked to one molecule of active ingredient.

The covalent linkage may, for instance, be through a peptide bond between a carboxyl group on one of the molecules and an amine group on the other, or may be via an ester linkage between a carboxyl group on one compound and a hydroxyl group on the other compound. Sometimes the linkage may be one which is capable of being lysed in the body, for instance within the tissue where the active ingredient has its effect. However such lysis is often unnecessary as the polysaccharide may not have a significant effect on the activity of the active ingredient. Another linkage by which the active ingredient could be covalently bonded to the polysaccharide compound is via a Schiff base, between an amino group on one of the compounds and an aldehyde group on the other compound.

A pharmaceutically active compound can be covalently linked to a sialic acid-containing polysaccharide, or a derivative thereof, for instance by formation of a Schiff base between a free amino group on the active ingredient being reacted with an aldehyde group formed at the non-reducing end of the polymer by periodate oxidation. Alternatively a free amine group on a pharmaceutically active compound may be reacted with the 1-carboxyl group of the sialic acid residue to form a peptidyl bond. Alternatively, an ester linkage can be formed between the 1-carboxylic acid group and a hydroxyl or other suitable active group on an active ingredient. Alternatively, a carboxyl group on a pharmaceutically active compound may form a peptide linkage with deacetylated 5-amino group. Alternatively, an aldehyde group of a molecule of a pharmaceutically active compound may form a Schiff base with the N-deacetylated 5-amino group of a sialic acid residue. Difunctional linking compounds may be used, for instance to link amine and thiol groups, or to link two hydroxyl groups.

Alternatively, the polysaccharide compound may be associated in a non-covalent manner with the pharmaceutically active compound. For instance the polysaccharide compound and the pharmaceutically active compound may be linked via hydrophobic interactions, for instance via lipid components of the polysaccharide compound with a hydrophobic pharmaceutically active compound. Other non-covalent associations may be via electrostatic interactions, with oppositely charged ions attracting each other. For instance a positively charged active ingredient, for instance comprising quaternary ammonium ions, may be ionically linked with carboxylate groups on the polysaccharide. One example would be the antibiotic doxorubicin ionically linked to carboxylate groups of polysaccharide B.

In another embodiment of the invention, the polysaccharide compound may interact via a drug delivery system with the pharmaceutically active compound. For instance the polysaccharide compound may be used to affect the availability of the active ingredient in the circulation by affecting the recognition and take up of the conventional molecular or particulate components of DDS, of the type described above. In this embodiment, the polysaccharide compound may be covalently linked or non-covalently associated with the particulate or molecular entity of the drug delivery system. For instance the polysaccharide compound may act in a manner analogous to the action of polyethylene glycol and/or the Pluronic copolymer type materials discussed above.

Examples of covalent interactions between the polysaccharide compound and a liposome could be via phosphate ester linkages between the glycerophosphate head groups of the phospholipids. The covalent bonds may be formed either before or after formation of the phospholipids into vesicles. Alternatively, the polysaccharide may be linked to lipid components via interactions between the 1-carboxylic acid group of sialic acid, hydroxyl groups on the polysaccharide or amine groups produced by deacetylation and reactive groups on molecules including hydrophobic chains. For instance the hydrophobic molecules may be lipids, especially phosphatidyl ethanolamine derivatives, to the amine group of which covalent linkages may be formed. Likewise covalent interactions between nonionic synthetic surfactant vesicles and polysaccharide compounds may be via ester, amide or ether linkages onto the hydrophilic portions of the molecules, formed either before or after formation of the vesicles.

Alternatively, the polysaccharide compound may be non-covalently linked to a PDDS component. Non-covalent linkages may for instance be hydrogen bonding interactions between hydrophobic portions of the PDDS component and a polysaccharide compound which comprises a hydrophobic group (eg which is a glycolipid) or which has been covalently linked to a hydrophobic group. Such hydrophobic derivatives of the polysaccharide compound may be formed by reacting the 1-carboxylic acid group of a sialic acid residue in the polysaccharide compound or a hydroxylic group of the polysaccharide compound or an aldehyde derivative of a polysaccharide molecule, for instance with a hydroxyl group, a carboxylic acid group, a halogen atom or an amine group. For instance a glycolipid compound may be incorporated into the shell of a liposome or surfactant vesicle, with its fatty acid hydrophobic chain portions interacting with the hydrophobic portions of the lipids or surfactants. Polysaccharides B, K92, for instance, would be suitable for use in this application. The glycolipid would conveniently be incorporated with the surfactants or phospholipids whilst the vesicles were being formed or after formation of the vesicles by equilibration of glycolipid with preformed liposomes.

Where the DDS comprises a macromolecular component such as an antibody, neoglycoprotein or synthetic polymer, the polysaccharide component may be covalently or non-covalently associated with the macromolecular component. Covalent linkages could be via ester, peptide or other linkages of the type described above for linkages between pharmaceutically active compounds and the polysaccharide compound, and are most conveniently via peptide linkages with carboxyl or amine groups on the peptide portion of the macromolecule.

Many examples of processes for producing covalent linkages between polysaccharides and other compounds, such as proteins, peptides or lipids are known, and can be used to achieve the covalent bonds suggested above. For instance reducing sugars can be linked to amine groups, for instance of the N-terminal of a peptide, of side chains of lysine-containing peptides or of ethanolamine groups of lipids, by a reactive amination procedure as described by Gray G, Arch. Biochem. Biophys. 163 426 (1974) followed by a selective reduction of the enamine intermediate by cyanohydridoborate anion as described by Borch R F et al in J. Am. Chem. Soc. 93, 2897 (1971) to form a secondary amine. Non-reducing sugars including sialic acid residues can first be derivatised by selective oxidation using periodate, as described by Jennings H J et al. J. Immunol. 127, 1011 (1981) to form an aldehyde group, before being coupled in the reaction amination procedure.

An alternative reaction couples the carboxylic acid group of a saccharide unit, such as of sialic acid, to an amine group, for instance of the N-terminal of a peptide or the side chain of a lysine residue, in the presence of a carbodiimide, based on the method described by Weissig V. et al, FEBS Letts. 202, 86 (1986). Of course this method could also be used to couple a 5-deacetylated amine group of a sialic acid unit to a carboxylic acid group eg in a protein side chain or C-terminal.

An alternative reaction involves the diazotisation of an aromatic amine group introduced into the polysaccharide for instance using para-phenylenediamine reacted onto a carboxylic acid group, followed by the reaction with the side chain of a phenylalanine or tyrosine residue of the protein similar to the technique developed by Snyder S L et al. Biochim. Biophys. Acta, 772, 288 (1984) and modified by Senior et al BBA 1003, 58, (1989).

Free hydroxyl groups on a polysaccharide compound can be linked to free hydroxyl groups or thiol groups on a protein or lipid for instance by esterification using a dibasic acid or acid derivative.

Where the compound to be coupled to the carbohydrate moiety contains (or can be derivatised, eg via an aryl group, to contain) an isothiocyanate group, this can be coupled to a free hydroxyl group of the polysaccharide for instance by reaction in methyl sulphoxide, catalysed by dibutyl tin dilaurate, by the method described by de Belder et al in Carbohydrate Res. (1973), 30, 375–378. The product is a thiocarbamoyl derivative. for instance fluorescein isothiocyanate may be reacted to form an O-(fluoresceinylthiocarbamoyl) sialic acid derivative.

Alternative reactions of sialic acid-containing polysaccharide involve partial de-acetylation, that is removal of some of the N-acetyl groups, to reveal free amine groups, followed by reaction of these amine groups by covalent coupling reactions as described above. A further reaction made possible by this preliminary deacetylation is the reaction with hetero-bifunctional reactant such as the N-hydroxysuccinimide ester of iodoacetic acid, N-succinimidyl-4-(2-bromoacetylamino)benzoate or N-succimimidyl-3-(2-pyridyldithio) propionate followed by the coupling to the thiol group of a peptide or protein, as described by Wolff and Gregoriadis in Biochim. Biophys. Acta (1984) 802, 259–273 and Barbet et al in J. Supramol. Struct. Cell. Biochem. (1981) 16, 243–258.

Where the polysaccharide compound is used to coat a liposome, it may be incorporated as the liposome is formed for instance by mixing an anchored polysaccharide compound, that is, provided with a hydrophobic anchor moiety, with the liposome-forming lipid. Alternatively, the polysaccharide compound can be post reacted onto the surface of preformed liposome, by reaction with active groups on the liposome surface, such as amine groups, aromatic amine groups, carboxylic acid groups or derivatives such as acid chloride groups. For instance Weissig V et al (op cit) describe an anchor which is the N-glutaryl derivative of phosphatidyl ethanolamine. The carboxylic acid group can be reacted with amine groups on a polysaccharide compound, for instance of a deacetylated or partially deacetylatd polysialic acid compound in the presence of a carbodiimide. Alternatively, palmitoyl or other fatty acid chloride can be used to react with amine groups on a polysaccharide compound. The 1-carboxylic acid group of a sialic acid residue can be used to form an ester linkage with a hydrophobic group-containing compound having a hydrocarbyl-halogen atom, by formation of the crown ether of the sodium salt of the carboxylic acid followed by reaction with the halo-hydrocarbon. Many other methods of binding proteins, which can be easily adapted to binding of polysaccharides, to liposomes and lipids have been described and are reviewed by Gregoriadis, G. ed "Liposomes as drug carriers" John Wiley & Sons (1988), Heath T et al Chem. Phys. Lipids 40, 347 (1986) and Machy, P. et al "Liposomes in Cell Biology and Pharmacology" Les Editions Inserms, Paris (1987).

According to a further aspect of the invention, there are provided new liposomes having bound to their external surface a polysaccharide moiety which comprises at least 5 sialic acid units per molecule. The liposomes can be used in a method of treatment by therapy or diagnosis.

According to a further aspect of the invention, there is provided new method of producing liposomes from a mixture of liposome-forming lipids and a polysaccharide compound comprising a polysaccharide component containing at least 5 sialic acid units per moleule and a hydrophobic portion.

In these further aspects of the invention, the polysaccharide can be incorporated into the liposomes by any of the methods described above. Where the polysaccharide compound used to make the liposomes is other than a naturally occurring glycolipid whose compound preferably has the hydrophobic portion covalently bound to a sialic acid unit of the polysaccharide component, for instance through the 1-position or the nitrogen atom. A link through the 1-position may for instance comprise an ester linkage. These polysaccharide compounds are believed to be new and form a further aspect of this invention.

An ester linkage at the 1-position may be formed by a new process comprising a first step in which a crown ether is reacted with a compound comprising a polysaccharide moiety including at least 5 sialic acid residues per molecule in the form of an alkalimetal or ammonium salt and a second step in which the product of the first step is reacted with a compound of the formula X-$R^1$ where $R^1$ is an optionally substituted $C_{8-30}$-alkyl or -alkenyl group and X is a halogen atom. X is preferably bromine. The first step of the reaction may for instance be carried out in aqueous solution, for instance of the sodium salt of the polysaccharide (i.e. of the sialic acids' carboxylic groups), in the present of a crown ether such as 18-crown-6. Following reaction, for instance at ambient temperature until reaction is complete, (eg for a few minutes up to a few hours eg, 5 mins–5 hours) water is removed for instance by evaporation or, preferably, by freeze drying. The crown ether is then for instance redissolved in an organic solvent, conveniently dimethylformamide, followed by addition of a halohydrocarbon or substituted compound and stirring until reaction has taken place, at raised or, preferably ambient temperature, eg for a few hours or days, for instance 5 hours–5 days. The alkyl or alkenyl group of the compound X R$^1$ is usually a $C_{12-24}$, preferably $C_{14-22}$-alkyl or -alkenyl, which may optionally include substituents such as alkyl or -alkenyl groups, alkanoyloxy or alkylcarboxamido in each of which the alkyl or alkenyl groups have 6 to 30 carbon atoms.

In the broad aspect of the present invention, where the polysaccharide is linked directly to a molecule of an active ingredient via a covalent bond, there may be a single molecule attached to each molecular of active ingredient, for instance where the active compound is a small molecule, or a relatively short polypeptide. Where a single molecule of polysaccharide is linked it is particularly valuable for the molecule to be formed of at least 50 sialic acid units and preferably about 100 sialic acid units or more. Where the polysaccharide is linked to the active ingredient via a DDS or directly via a covalent linkage to an active ingredient which is a relatively large molecule, for instance a protein or a polypeptide, then more than one molecule of polysaccharide may advantageously be associated with DDS unit or each molecule of of active ingredient as the case may be. Where the polysaccharide comprises a relatively low number of sialic acid units, for instance less than 50 or 20 units, it is preferred for several molecules to be associated with each DDS unit or molecule of active ingredient. Often it is advantageous for several molecules having a relatively high number of sialic acid units, for instance more than 50 or about 100 or more, to be associated with each DDS unit or active ingredient molecule. The total number of sialic acid units associated with each DDS unit or active ingredient molecule affects the total hydrophilicity imparted to the active ingredient. By the use of relatively high molecular weight polysaccharide molecules, there is steric effect at increased distances from the active ingredient or DDS which is thought to increase the half life in the circulation and stability and to reduce the immunogenicity of the active ingredient. Where a high molecular weight polysaccharide compound is used more than one molecule of active ingredient can be associated with each moleule of polysaccharide compound especially where the active ingredient has a relatively low molecular weight, for instance when it is a peptide.

The present invention is of particular value where the pharmaceutically active compound is one which needs to be available in the circulation of a patient for an extended period. It is of particular use for pharmaceutically active ingredients which comprise proteins formed from recombinant DNA technology, which tend to be taken up rapidly by tissues, where their pharmaceutical activity is not exhibited. Pharmaceutically active compounds whose availability in the circulation would be beneficially prolonged by the invention are interleukins, for instance IL-2, IL-6 or IL-1 interferons, tumour necrosis factor (TNF) as well as enzymes for instance for use in enzyme therapy as described by Abuchowski (op. cit.) etc. Another class of compounds which may be beneficially used in the invention are compounds which compete with viruses, for instance HIV, for interaction with certain receptors present on cells in the bloodstream. One type of active compound which may be used in the invention is fluorescent agents which can be used in clinical investigations. For instance fluorescein derivatives may be directly coupled to a polysaccharide compound or may be incorporated into liposomes which are coated with polysaccharide compound. Active ingredients which would usefully be incorporated into liposomes or other DDS include cytostatics, cytokines, antibiotics, haemoglobin, enzymes, hormones, steroids etc.

The following examples illustrate the increased circulation time of a molecule used as a model for an active ingredient in a mouse, used as a model for all mammals. It is to be expected that the same effects will be observed where active ingredients are combined with the polysaccharide compound and administered to humans.

DESCRIPTION OF DRAWINGS

FIG. 12 shows coupling of N-tetradecyl-(2-bromohexadecyl carboxamide) with colominic acid crown ether.

EXAMPLES

Polysaccharide Compounds

Group B Polysaccharide

Figure 1:
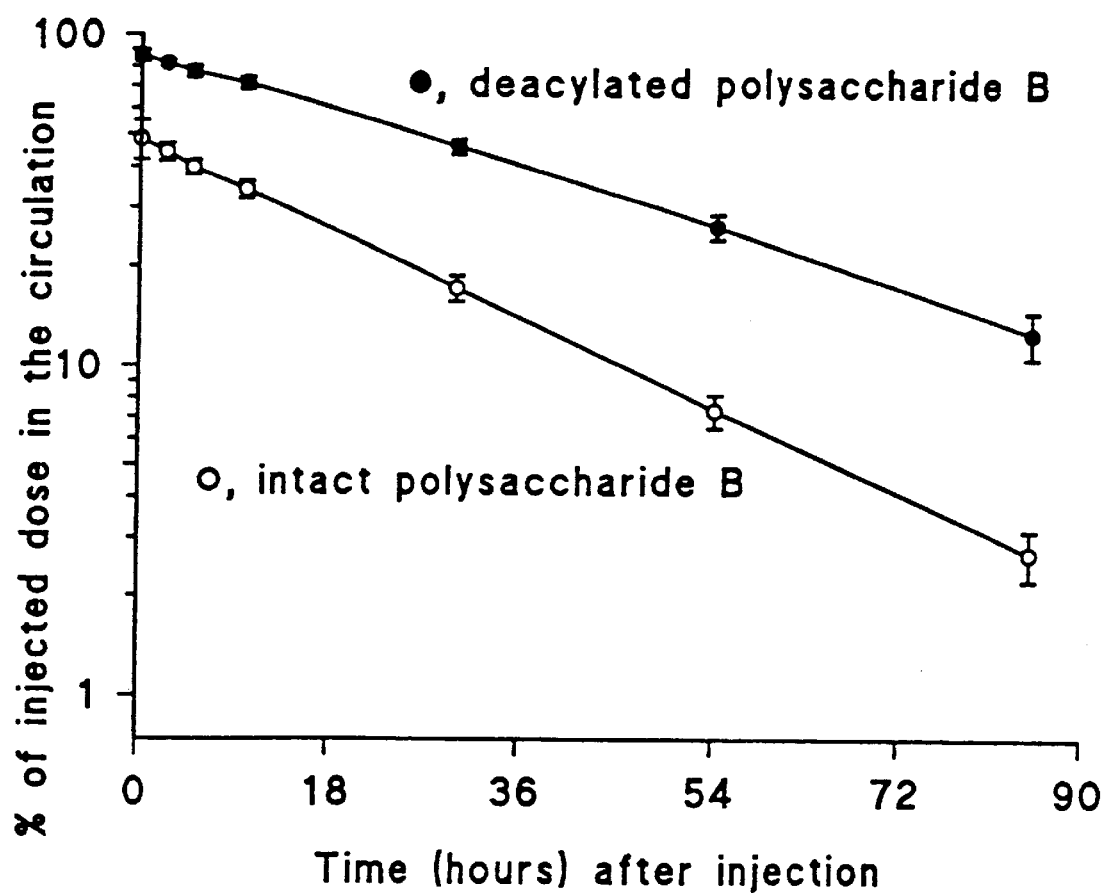
FIG. 1 shows the half life of polysaccharide B after intravenous injection.

Group B polysaccharide of *N. meningitidis* is a polymer made up of (2→8) α-linked sialic acid residues with chain length of about 200 residues (sialic acid units) and a terminal unit of phospholipid at the reducing end of the polymer. The polysaccharide is extracted from the cell wall of the bacteria *Neisseria meningitidis*. In aqueous solution, polymer forms aggregates (aggregated or intact form). Treatment of the solution with 0.1M NaOH at 37° for 4 hours removes the acyl chains of the phospholipid and the polymer chains deaggregate (deaggregated form).

Polysaccharide B from *E. Coli* K1 is a homopolymer of sialic acid linked 2→8 and having about 190 sialic acid units. *E. Coli* K1 is slightly pathogenic. It is referred to as "K1" in the following examples.

Polysaccharide B can be autohydrolysed by treatment at 100° C. pH 7.0 for 1–9 h to form a lower molecular weight polymer having a chain length which is probably less than 80 units. The polysaccharide is referred to as "lower molecular weight (mw) Dolysaccharide" in the following examples.

Polysaccharide B from *E. Coli* K1 can be hydrolysed to yet shorter chain lengths to form a product known as colominic acid having an average chain length of about 15–30 units. This is available commercially. The colominic acid used in these experiments was obtained from Sigma Chemical Co.

Polysaccharide K92 from *E. Coli* K92 is a glycolipid the polysaccharide moiety of which is a homopolymer of sialic acid 2→8 alternating with 2→9 linkages having a chain length of about 80 to 100 units. It is referred to as "K92" in the following examples. E. Coli K92 is substantially, non-pathogenic. The phospholipid moiety can be removed by hydrolysis as for N. meningitidis polysaccharide B.

Polysaccharide C from Neisseria meningitidis group C is a homopolymer of 2→9 linked sialic acid units, the chain length being about 120 units. It is a glycolipid and the phospholipid moiety can be removed as for N. meningitidis polysaccharide B.

Fluorescein conjugation

Fluorescein is used as an agent in clinical tests and as such is a pharmaceutical compound eg to investigate permeability and microcirculation in vivo. Fluorescein isothiocyanate (FITC) is used in some of these experiments to investigate the effect of conjugation of polysaccharide on the rate of clearance of fluorescein from the circulation (of mice). Fluorescein can be radiolabelled using $^{125}I$ by well known techniques. The "hot" fluorescein $^{125}I$ can subsequently be assayed by detecting the presence of the $^{125}I$ radio label. FITC is linked to the polysialic acid polysaccharide compound by forming the tetrabutylamino salt of the polysaccharide. This salt is then reacted with FITC in solution in DMSO/pyridine with stirring for 24 hours at room temperature using a technique originally described by A. N. de Belder et al Carbohydrate Res. 30, 375 (1973). The basic reaction is as follows:

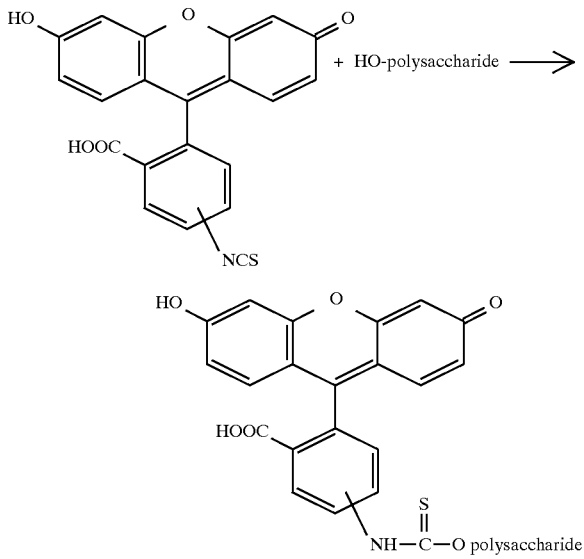

The conjugate which contains 0.93 nmol, FITC per/50,000 daltons of B polysaccharide is recovered by extraction of unbound FITC by dialysis, followed by ethanol precipitation of the conjugate, and gel filtration and finally reprecipitating the product in ethanol again. $^{125}I$-labelling is carried out after the conjugation.

It is known from the art that non-conjugated fluorescein is substantially cleared from the circulation within about 5 minutes.

Assay for Polysialic acid

In order to assay for polysialic acids including group B polysaccharide (PSB) in a blood sample, a sample of plasma is first treated by trichloroacetic acid (10% final concentration) to precipitate serum proteins many of which also contain sialic acid as terminal groups of the proteins. The treated serum is then assayed by a slight modification of the method of Svennerholm in Biochim. Biophys. Acta, vol. 24, pages 604–611, (1957). This measures polymeric sialic acid or other sialic acid as follows: the sample (0.5 ml) containing polysaccharide is mixed with Resorcinol reagent (0.5 ml) and heated in vigorously boiling water for 30 min. The sample is cooled and either read directly at 570 nm or the colour extracted with amyl alcohol (1 ml) and read at 590 nm. Standard curves were created by adding known amounts of the appropriate polysaccharide to serum, which was otherwise treated in the same manner to precipitate out serum proteins as described above, and analysing them by the calorimetric method described above.

Example 1

Half-life of polysaccharide B after intravenous injection

T.O. outbred mice weighing 25–30 g were injected intravenously (tail vein) with 0.2 ml pH 7.4 phosphate buffered saline containing 1.4 to 2.8 mg N. meningitidis group B polysaccharide in the aggregated or the deaggregated form. Animals were bled from the tail vein immediately before and at time intervals after injection and blood serum samples assayed for group B polysaccharide. The assay involves measurement of sialic acid by a calorimetric method after precipitation of serum proteins many of which also contain sialic acid and would otherwise interfere with the method. Group B polysaccharide values in sera were plotted in logarithmic graph and half-lives of the polymer injected as aggregated or deaggregated were derived. The results are given in the following table 1 and illustrated graphically in FIG. 1.

TABLE 1

| Time after Injection | Deacylated polysaccharide (% of injected)* | Intact polysaccharide (% of injected)* |
|---|---|---|
| 2–4 min | 90.0, 88.5, 87.1, 84.5, 81.02 | 40.0, 45.5, 48.0, 51.1, 57.8 |
| 2.5 hours | 81.0, 79.5, 82.3, 84.1 | 40.5, 42.6, 44.5, 46.1, 47.4 |
| 5.0 hours | 81.0, 79.1, 76.0, 76.5, 73.0 | 37.4, 38.8, 39.2, 41.0, 42.3 |
| 10.0 hours | 70.1, 67.2, 71.5, 72.2, 75.0 | 31.2, 32.6, 34.6, 35.5, 36.1 |
| 30.0 hours | 45.0, 43.2, 44.1, 47.5, 49.0 | 15.5, 16.3, 16.9, 17.8, 19.5 |
| 54.0 hours | 23.5, 25.0, 26.4, 27.5, 29.3 | 6.3, 6.6, 7.4, 7.9, 8.3 |
| 85.0 hours | 10.5, 11.1, 12.1, 13.7, 15.5 | 2.3, 2.4, 2.4, 3.1, 3.3 |

*Pairs of T.O. mice in 5 individual experiments were injected intravenously with 0.2 ml of 1% NaCl in PBS containing 1.4–2.8 mg PSB, intact or deacylated, respectively. Mice were bled at time intervals from the tail vein and blood plasma assayed for polysaccharide B. Results are expressed as % of the injected dose per total mouse blood. The numerical results in Table 1 show that 40.0 to 57.8% of the injected polysaccharide remains in the circulation within 2–4 mins of injection i.e. 42.2 to 60% of the injected dose of the aggregated polysaccharide is removed from the circulation within 2–4 min after injection. Thereafter, elimination rate is slow exhibiting a half-life of about 20 hours. The initial rapid removal of the polysaccharide is probably due to it being in the aggregated form with the formed particles trapped by the lungs or the RES on first passage. In contrast, only 10–19% of the deaggregated polysaccharide were removed by tissues during the first 2–4 min after injection. The remainder of the dose was eliminated slowly with a half-life of about 30 hours.

Pairs of T.O. mice in 5 individual experiments were injected intravenously with 0.2 ml of 1% NaCl in PBS containing 1.4–2.8 mg PSB, intact or deacylated, respectively. Mice were bled at time intervals from the tail vein and blood plasma assayed for polysaccharide B. Results are expressed as % of the injected dose per total mouse blood. The numerical results in Table 1 show that 40.0 to 57.8% of the injected polysaccharide remains in the circulation within 2–4 mins of injection i.e. 42.2 to 60% of the injected dose of the aggregated polysaccharide is removed from the circulation within 2–4 min after injection. Thereafter, elimination rate is slow exhibiting a half-life of about 20 hours. The initial rapid removal of the polysaccharide is probably due to it being in the aggregated form with the formed particles trapped by the lungs or the RES on first passage. In contrast, only 10–19% of the deaggregated polysaccharide were removed by tissues during the first 2–4 min after injection. The remainder of the dose was eliminated slowly with a half-life of about 30 hours.

The long half-life (30 hr) and the linear (on a log scale) rate of clearance from the blood circulation of almost all the injected amount of deaggregated group B polysaccharide suggest that the polymer (in the deaggregated form) is an excellent candidate to serve as a means of prolonging the circulation of drugs, peptides and proteins attached to it covalently. The polymer could also serve as coating material for drug-containing or drug-linked DDS or PDDS to prolong their half-life in the circulation. Also the aggregated (glycolipid) form may be useful in increasing the half life of phospholipid-vesicle PDDS.

Example 2

Clearance of intact low mw PSB conjugated to fluorescein from the blood circulation: the effect of dose T.O mice were injected intravenously with 0.2–0.25 ml phosphate buffered saline (PBS) containing intact "low" molecular weight polysaccharide B conjugated to fluorescein which was subsequently radiolabelled with $^{125}$I. Animals were bled at time intervals and $^{125}$I radioactivity measured in the plasma. Values are from individual animals and represent % of injected radioactivity in total blood (estimated at 7.5% of body weight). The dose column shows the total amount of cold (non-radioiodinated) and hot (radioiodinated) FITC-Polysaccharide-B conjugate mixed before injection. Numbers in parentheses signify the amount (μg) of radioiodinated conjugate in the mixture.

Figure 2:
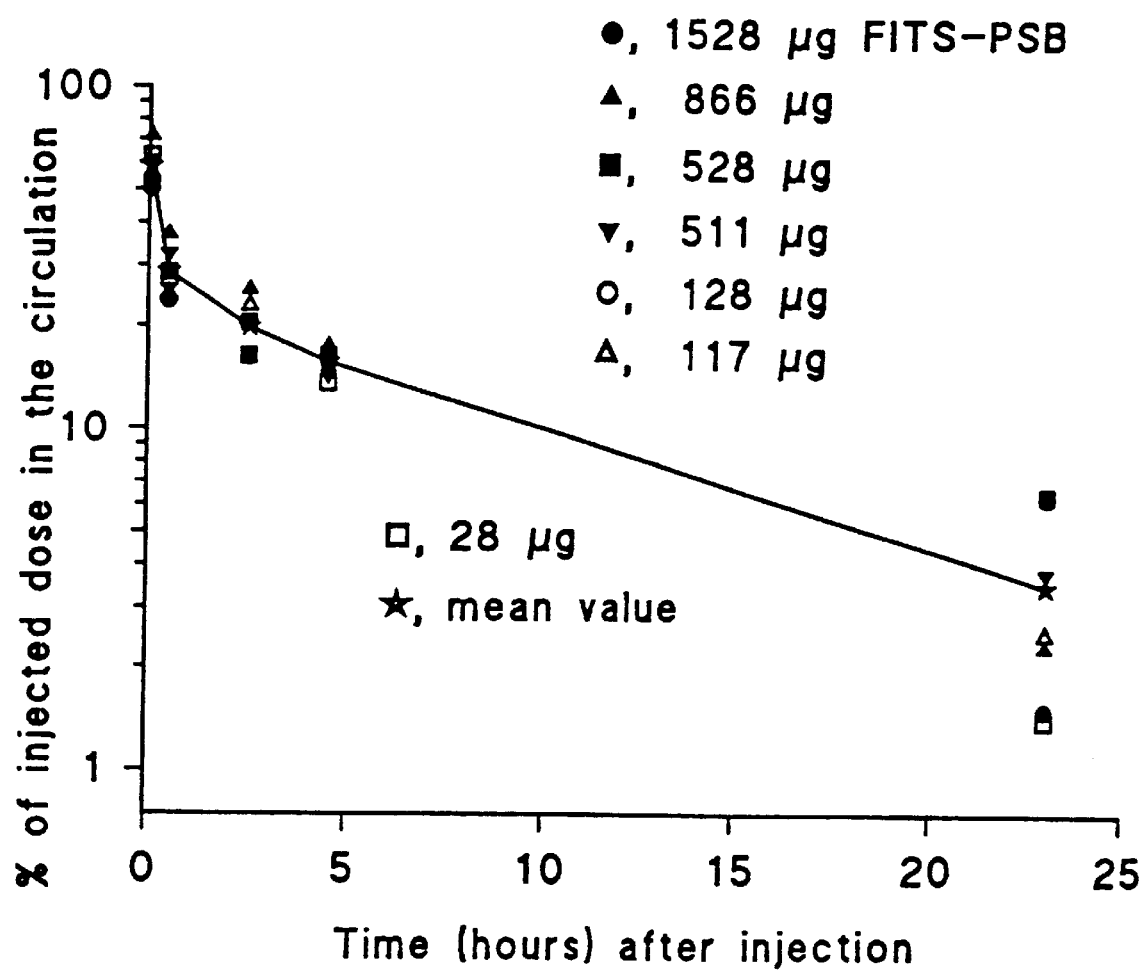
FIG. 2 shows clearance of low MW PSB conjugated to fluorescein from the blood.

The results are shown in the following table 2 and illustrated graphically in FIG. 2.

TABLE 2

| Dose μg total (hot) | % of injected dose in the circulation | | | | |
|---|---|---|---|---|---|
| | 2 min | 30 min | 2 h + 30 min | 4 h + 30 min | 23 h |
| 1528 (28) | 50.3 | 23.7 | 16.2 | 15.7 | 1.5 |
| 866 (6) | 71.6 | 37.0 | 25.5 | 17.4 | 2.3 |
| 528 (28) | 52.0 | 28.6 | 16.3 | 16.3 | 6.4 |
| 511 (11) | 60.7 | 32.4 | 20.5 | 14.3 | 3.8 |
| 128 (28) | 52.7 | 26.8 | 16.3 | 15.6 | 6.3 |
| 117 (17) | 52.0 | 24.7 | 22.8 | 16.3 | 2.5 |
| 28 (28) | 65.5 | 26.4 | 18.5 | 13.5 | 1.2 |
| 28 (28) | 59.5 | 28.8 | 22.4 | 13.7 | 1.6 |

The results show that conjugated fluorescein is cleared from the circulation relatively slowly compared to the known clearance rate of non-conjugated fluorescein. The low-molecular weight polysaccharide conjugation results in about 70% of the FITC conjugate being cleared from the circulation within 30 minutes from injection. Subsequently, the half life is about 6 hours and is independent of the dose. This latter fact indicates that there is no "saturation concentration" which might prevent the polysaccharide being effective for prolonging the circulation time for some active ingredients which need to be administered in relatively high doses i.e. when there will be a high dose of polysaccharide. Another advantage is that very little polysaccharide can be used to prolong the circulation of an active ingredient. Furthermore, since the rate is not affected by the ratio of hot FITC to total FITC, we are not simply measuring the rate of clearance of hot FITC which would be different than that of cold FITC.

Example 3

Deacylated low molecular weight polysaccharide B (*N. meningitidis*) conjugated to fluorescein clearance from the blood: the effect of dose T.O. mice were injected intravenously with 0.2–0.25 ml PBS containing hydrolysed (deacylated) "low" molecular weight polysaccharide B conjugated to FITC which was subsequently radiolabelled with $^{125}$I. Hydrolysis (4 h at 37° at pH 8.0) to remove the acyl groups of the phospholipid was carried out using the FITC-polysaccharide B conjugate mixed with the radioiodinated conjugate.

Figure 3:
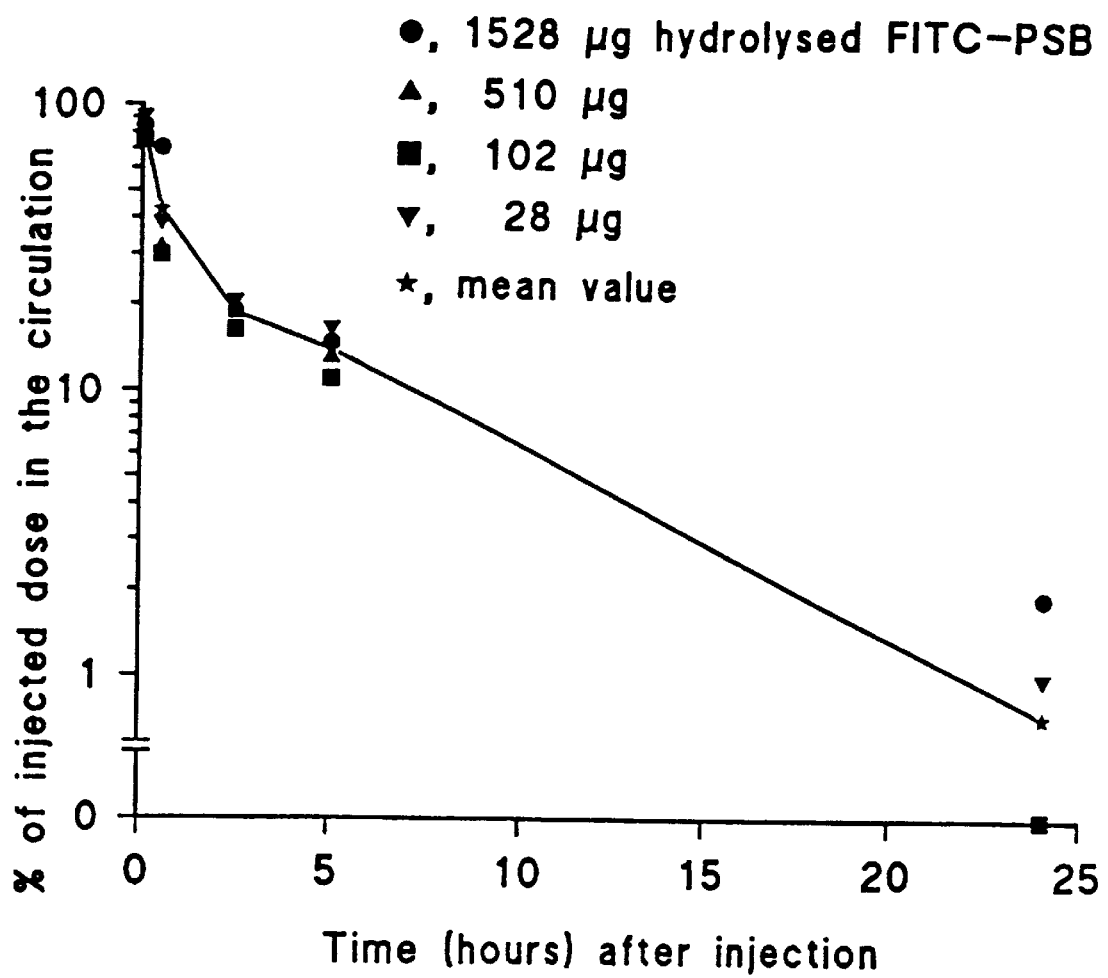
FIG. 3 shows clearance of low MW polysaccharide B (*N. meningitidis*) conjugated to fluorescein from the blood.

The results are shown in the following table 3 and in FIG. 3.

TABLE 3

| Dose (μg) | % of injected dose in the circulation | | | | |
|---|---|---|---|---|---|
| | 2 min | 30 mins | 2 h + 30 min | 5 h | 24 h |
| 1528 (28) | 84.2 | 70.7 | 19.0 | 14.7 | 1.9 |
| 510 (10) | 75.6 | 31.4 | 18.6 | 13.0 | 0.0 |
| 102 (2) | 75.2 | 29.8 | 16.3 | 11.0 | 0.0 |
| 28 (28) | 92.0 | 39.0 | 20.8 | 16.6 | 1.0 |

The results indicate that, similar to the results for Example 2, conjugation with this polysaccharide compound, which is similar to that used in Example 2 but has had the phospholipid moieties deacylated by hydrolysis, results in only 29.3–70.2% of the FITC-conjugate being removed from the circulation within the first 30 minutes or so after injection, and the subsequent half life being about 5½ hours. The deacylation of the phospholipid portion seems to have little effect on the properties of the polysaccharide compound in so far as increasing the circulation time is concerned except for the first few minutes when concentration is higher for the corresponding time for the deacylated polysaccharide (table 3) and this is possibly because, following the hydrolysis of the native polysaccharide to form shorter chain lengths, only a minority of the polysaccharide molecules have a phospholipid chain attached. Deacylated of the phospholipid thus affects a minority of molecules.

Example 4

Clearance of polysaccharide C (PSC) (*N. meningitidis*) from the circulation after intravenous injection The method of example 1 was followed but using *N. meningitidis* polysaccharide C. The intact polysaccharide and the hydrolysed form in which the phospholipid groups were deacylated were compared.

T.O. mice were injected i.v. with 1250 μg polysaccharide C (PSC) either intact or hydrolysed to deacylate the phospholipid. Animals were bled at time intervals and plasma samples analysed for N-acetyl neuraminic acid (NaNa) (sialic acid). Results from individual animals are % of injected material per total blood.

Figure 4:
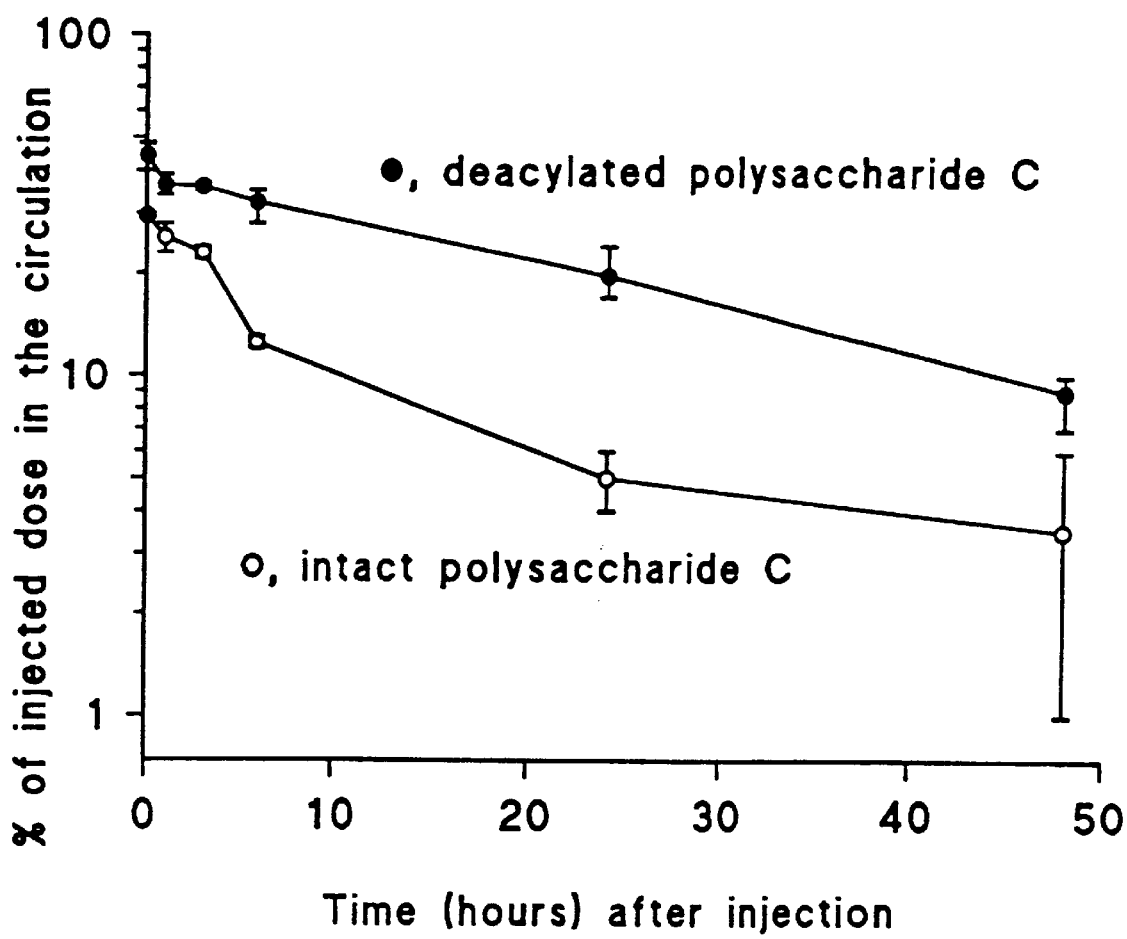
FIG. 4 shows clearance of low MW polysaccharide C (PSC) (*N. meningitidis*) from circulation after injection.

The results are shown in the following table 4 and graphically in FIG. 4.

TABLE 4

| Material injected | % of injected dose remaining in the circulation | | | | | |
|---|---|---|---|---|---|---|
| | 2 min | 1 h | 3 h | 6 h | 24 h | 48 h |
| PSC (intact) | 29 | 23 | 24 | 13 | 4 | 1 |
| PSC (intact) | 30 | 28 | 22 | 12 | 6 | 6 |
| PSC (hydrolysed) | 48 | 36 | — | 35 | 18 | 10 |
| PSC (hydrolysed) | 40 | 34 | 35 | 28 | 17 | 7 |
| PSC (hydrolysed) | 45 | 39 | 37 | 34 | 24 | 10 |

The results indicate, as for the results of Example 1 that for both intact and hydrolysed (deacylated) PSC a proportion of the polysaccharide compound is removed from circulation relatively quickly after injection, but thereafter the removal rate is slow. The rate of removal of intact polysaccharide is higher (i.e. the half life is lower) (8 h) than for the hydrolysed form (20 h) and the latter would be good candidate for use to prolong the circulation time of and stabilise active ingredients.

Example 5
Clearance of Rolysaccharide K92 from the circulation after intravenous injection The procedure of Examples 1 and 4 was repeated, but using polysaccharide K92, in its intact and hydrolysed (to deacylate the phospholipid groups) forms.

T.O. mice were injected i.v. with 1230 µg intact or hydrolysed (deacylated) polysaccharide K92 (PS K92). Animals were bled at time intervals and plasma samples analysed for N-acetyl neuraminic acid (NaNa). Results from individual animals are % of injected material per total blood.

Figure 5:
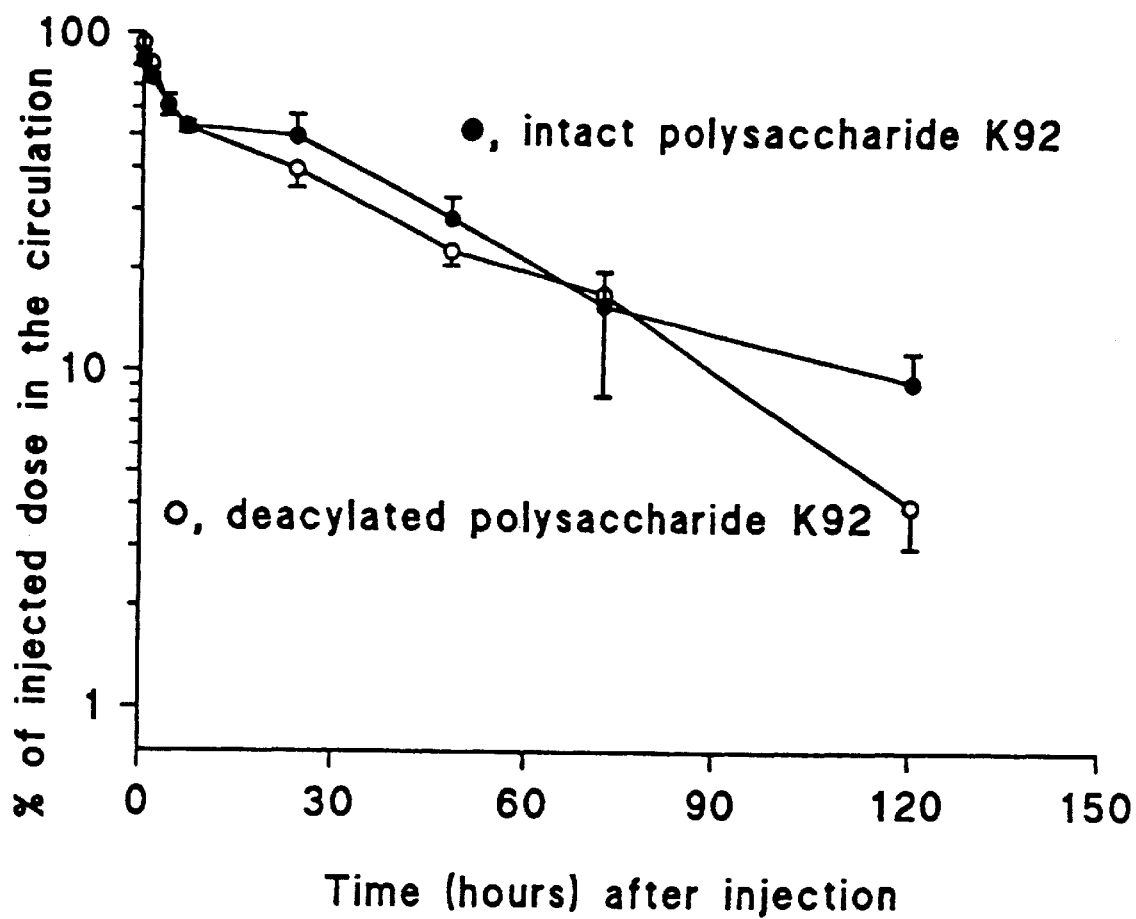
FIG. 5 shows clearance of polysaccharide K92 from circulation after injection.

The results are shown in the following table 5 and illustrated graphically in FIG. 5.

TABLE 5

| Material injected | % of injected dose remaining in the circulation | | | | | | | |
|---|---|---|---|---|---|---|---|---|
| | 2 min | 1 h + 20 min | 4 h | 7 h | 24 h | 48 h | 72 h | 120 h |
| PS K92 (intact) | 80 | 73 | 58 | 52 | 52 | — | 11 | 7 |
| PS K92 (intact) | 82 | 79 | 65 | 55 | 41 | 24 | 17 | 10 |
| PS K92 (intact) | 85 | 69 | 62 | 52 | 56 | 33 | 19 | 11 |
| PS K92 (hydrolysed) | 91 | 79 | 57 | 55 | 45 | 22 | 16 | 4 |
| PS K92 (hydrolysed) | 90 | 77 | 60 | 51 | 37 | 25 | 26 | 3 |
| PS K92 (hydrolysed) | 109 | 87 | 65 | 52 | 37 | 21 | 9 | 5 |

The results indicate that the initial loss in the first few minutes after injection for both these polysaccharide compounds is relatively low (compared to the other polysaccharide compounds tested). Furthermore the subsequent rate of removal from the circulation is very low, the half life in each case being about 40 hours. Thus even after 5 days there is still a significant proportion of the polysaccharide remaining in the circulation.

The removal of the acyl groups from the phospholipid moiety from this compound does not appear to make a significant difference to the half-life and it is not fully understood why this is the case. It might appear that the particular arrangement of the compound affects its properties so markedly that the presence of the phospholipid has little effect. These compounds would be expected to be of very great benefit for increasing the circulation time and stability of drugs and would provide them with good extended release characteristics, allowing for optimisation of targetting to organs or cells by targetting groups.

Example 6
Clearance of colominic acid and colominic acid-FITC conjugates from the circulation after intravenous injection The method of example 1 was repeated for intact colominic acid. FITC-colominic acid conjugate labelled with $^{125}$I was also administered in a separate set of experiments and the results assessed as in Example 2.

T.O. mice were injected i.v. with 1600 µg (FITC-colominic acid) or 1920 µg intact colominic acid. Animals were bled at time intervals and plasma samples analysed for NaNa. Results from individual animals are % of injected material per total blood.

Figure 6:
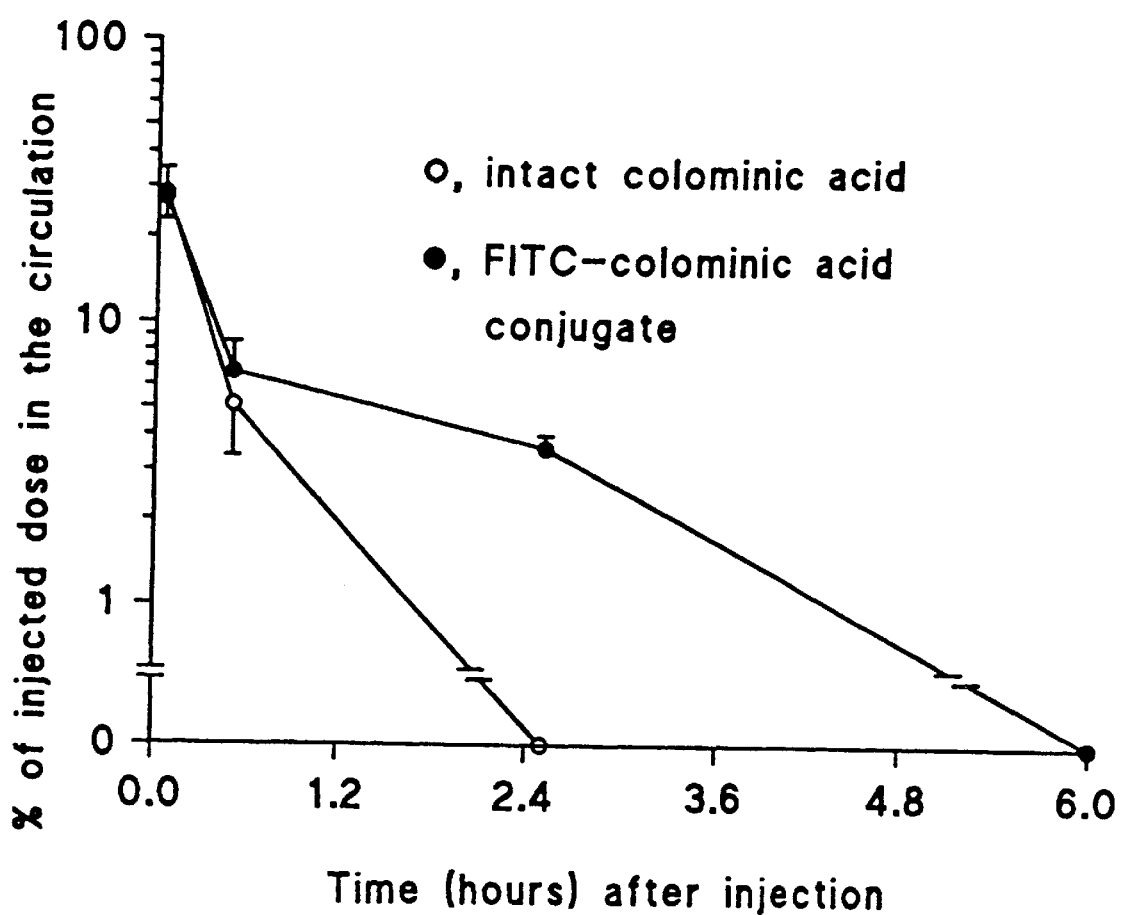
FIG. 6 shows clearance of colominic acid and colominic acid-FITC conjugates from circulation after injection.

The results are shown in the following table 6 and illustrated graphically in FIG. 6.

TABLE 6

| | % of injected dose remaining in the circulation | | | |
|---|---|---|---|---|
| Material Injected | 2 min | 30 min | 2 h + 30 min | 6 h |
| Colominic acid | 27.5 | 7.0 | 0.0 | 0.0 |
| Colominic acid | 23.4 | 4.7 | 0.0 | 0.0 |
| Colomonic acid | 34.0 | 3.6 | 0.0 | 0.0 |
| FITC-Colominic acid | 19.3 | 8.8 | 4.0 | 0.0 |
| FITC-Colominic acid | 28.9 | 5.8 | 3.6 | 0.0 |
| FITC-colominic acid | 34.0 | 5.4 | 3.2 | 0.0 |

The results indicate that the rate of removal from the circulation of the FITC-colominic acid conjugate is substantially the same as the rate of removal of colominic acid alone. Although the polysaccharide does have some effect in increasing the circulation time of FITC, the improvement is not as good as for the higher molecular weight polysaccharides which have longer half lives.

Example 7
Preparation of Colominic Acid-Lipid Derivatives
Material and Methods

Egg lecithin was purchased from Lipid Products, Nuthill, Surrey. Cholesterol, dichloromethane (DCM), dimethylformamide (DMF), chloroform and metanol were from E. Merck (Germany) and were used without further purification. Colominic acid sodium salt ((poly-2,8-N-acetylneuraminic acid) from *E. Coli* and Sephadex G-200 (coarse) were obtained from Sigma Chemicals, London. 18-Crown-6, 2-bromohexadecanoic acid, 1-tetradecylamine,1-bromooctadecane and 2,4,6 trichlorophenol were purchased from Aldrich Chemical Company and used without further purification.

Example 7.1
Synthesis of colominic acid conjugate with octadecane (scheme 1)

(a) Preparation of Colominic acid crown ether:

Colominic acid (sodium salt) (50 mg) was dissolved in 20 ml distilled water and 18-Crown-6 (30 mg) was added by stirring at 20° C. for 30 minutes. The water was evaporated by freeze-drying.

(b) Coupling of Colominic acid crown ether with 1-bromooctadecane (product D6):

Colomonic acid crown ether (35 mg) was dissolved in 1.5 ml DMF and 1-bromooctadecane (6 mg) was added by stirring at 20° C. for 24 h. The solvent was evaporated and the product redissolved in 1 ml distilled water. Removal of water was achieved by freeze-drying.

Example 7.2
Synthesis of colominic acid conjugate with N-tetradecylhexadecylcarboxamide (scheme 2)
Synthesis of N-tetradecyl-(2-bromohexadecyl carboxamide)

(a) Preparation of 2-bromohexadecanoic acid phenylester

2-Bromohexadecanoic acid (1 g) was dissolved in dry chloroform (20 ml). After addition of 2,4,6 trichlorophenol (0.558 g), the reaction mixture was placed in an ice bath. Dicyclohexylcarbodiimide (0.736 g) dissolved in dry chloroform (2 ml) was added to the solution. After stirring the solution for 15 minutes in an ice bath, the temperature was adjusted to 20° C. Formation of the product was ascertained by thin layer chromatography on silicic-acid plates with dichloromethane/methanol (10:0.1 v/v) mixture as solvent. The solution was stirred for 24 h at 20° C. and the precipitated urea removed by filtration. The filtrate was washed twice with sodium bicarbonate (0.05M) solution and water. The crude reaction product was purified by liquid chromatography on silica gel using the same solvent system as eluent.

(b) Preparation of N-tetradecyl-(2-bromohexadecyl carboxamide):

1-tetradecylamine (0.591 g) was added to a solution of 2-bromohexadecanoic acid phenyl ester (1.425 g) in dy chloroform by stirring at 20° C. for 24 h. Formation of the peptide bond was acertained by thin layer chromatography on silic-acid plates with dichloromethane/methanol (10:0.1 v/v) mixture as solvent. The reaction mixture was washed with citric acid solution (10%, w/v), sodium bicarbonate solution (0.05M) and water (×3).

(c) Coupling of N-tetradecyl-(2-bromohexadecyl carboxamide) with colominic acid crown ether (Product D11)

Colomonic acid crown ether (80 mg) was dissolved in dry dimethylformamide (DMF) (4 ml). After addition of N-tetradecyl-(2-bromohexadecyl carboxamide) (60 mg), the solution was stirred at 20° C. for 24 h. Then the solvent was evaporated under vacuum. The residue was dissolved in water (2 ml) which was then removed by freeze-drying.

Example 7.3
Incorporation of the Colominic acid-lipid derivatives onto liposomes To prepare small unilamellar liposomes (SUV) incorporating the derivatives, egg phosphatidylcholine (PC) (32 μmol) and cholesterol (32 μmol) in chloroform were mixed in a molar ratio of 1:1. Colominic acid-lipid derivatives synthesized as above (10% w/w of the total liposomal lipids) were dissolved in chloroform/methanol (1:1 v/v) and added to the lipid mixture. The solvents were driven off by using rotary evaporation under vacuun and the dried lipids were suspended in 2 ml of potassium phosphate buffer (pH 7.4, 0.1M) by gentle shaking. The milky suspension was sonicated in an ice bath for ten one minute periods alternating with 30 second intervals. After sonication, the samples were allowed to stand at 20° C. for 2 h. Non-incorporated materials were separated from liposomes by column chromatography on Sephadex G-200 pre-equilibrated with potassium phosphate buffer (pH 7.4, 0.1).

Determination of Colominic acid

Colominic acid was determined spectrophotometrically in 0.1 ml of the fractions obtained following chromatography using the general method described above. The extent (% of total used) of colominic acid incorporation into liposomes was estimated on the basis of total recovered in the fractions pertaining to the liposome peak and those collected subsequently (second peak of non-incorporated material).

Results
Characterisation of N-tetradecyl-(2-bromohexadecylgarboxamide):

The conjugation (scheme 2b) of 2-bromohexadecanoic acid with 1-tetradecylamine was ascertained by mass spectrometric analysis. Before coupling, an active ester of the 2-bronohexadecanoic acid was synthesized (scheme 2a). In the mass spectrum of the product, presence of the peak at 514 m/z indicates the formation of the bond between 2-bromohexadecanoic acid and 2,4,6 trichlorophenol. The product was then conjugated with 1-tetradecylamine, with the mass spectrum of the resultant material showing a peak at 530 m/z which implies that the conjugation of these two compounds was completed.

Liposome Characterisation:

Throughout the experiments, small unilamellar vesicles (SUV) were prepared with PC and cholesterol at a molar ratio of 1:1, colominic acid-lipid derivatives were added to lipid mixtures (10% of total lipid weight) when required. SUV were separated from the non-incorporated materials by molecular sieve chromatography using Sephadex G-200.

Figure 7:
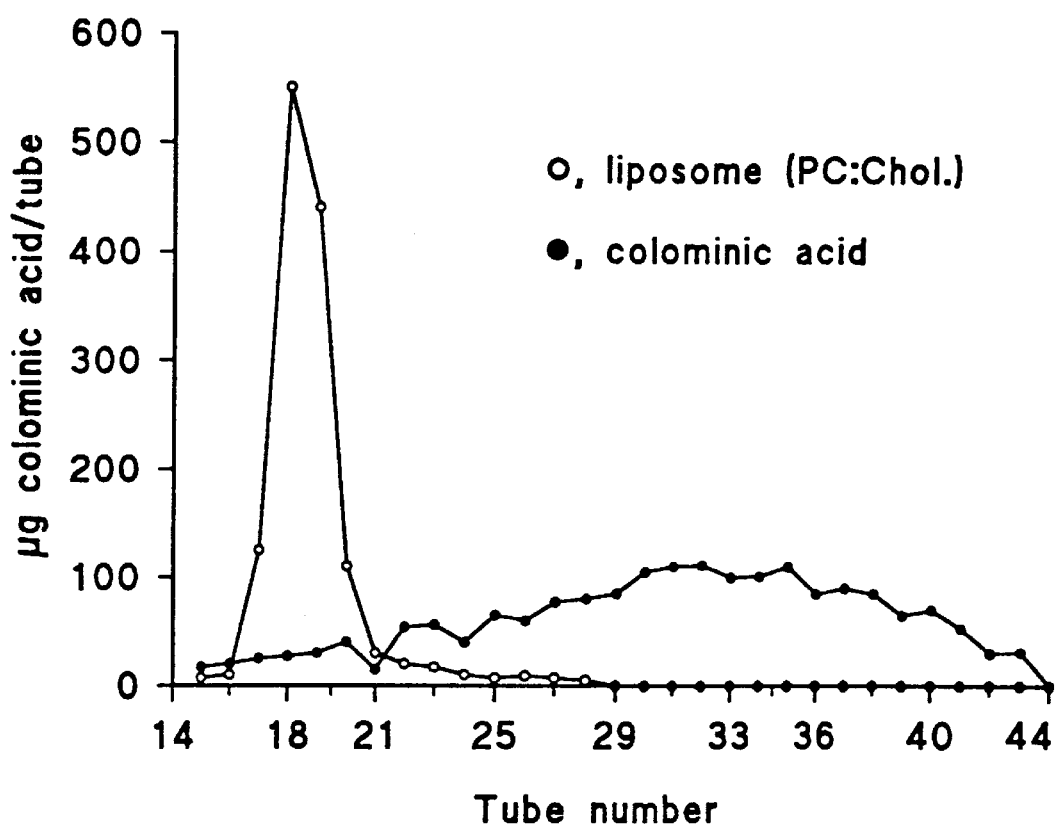
FIG. 7 shows elution profiles of colominic acid and SUV.
Figure 8:
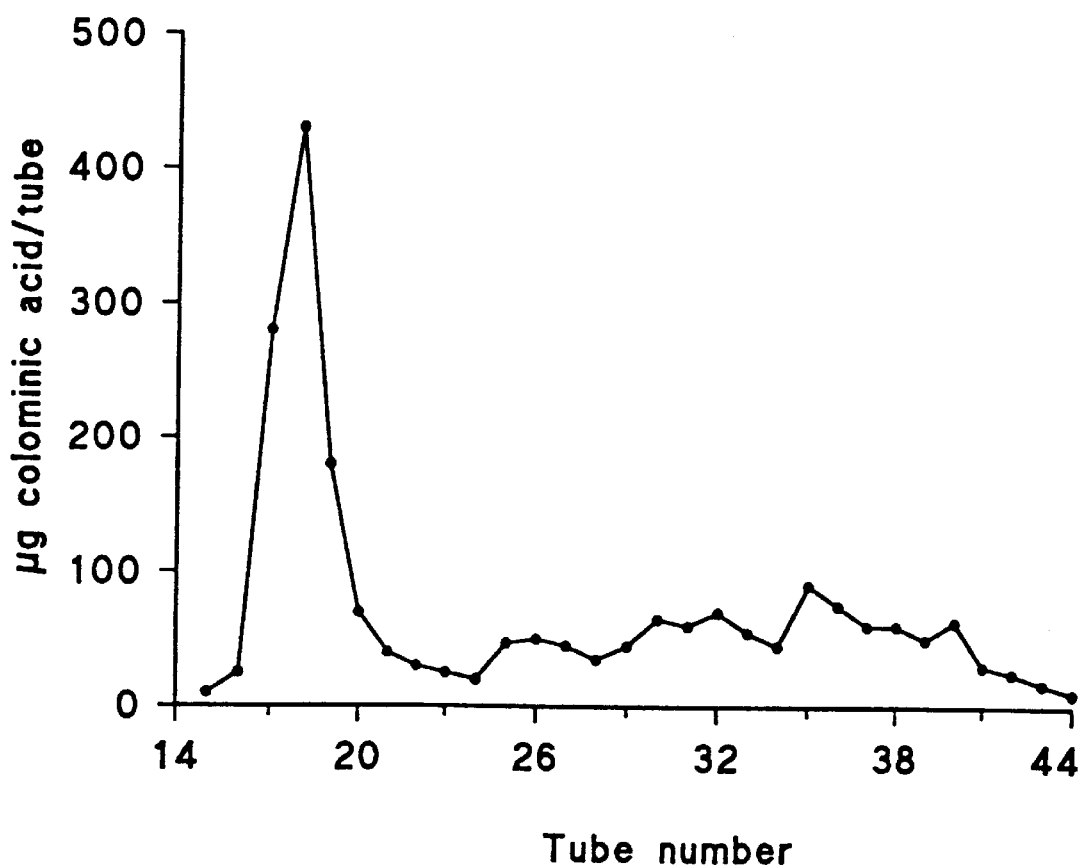
FIG. 8 shows elution profiles of liposomal $D_6$.
Figure 9:
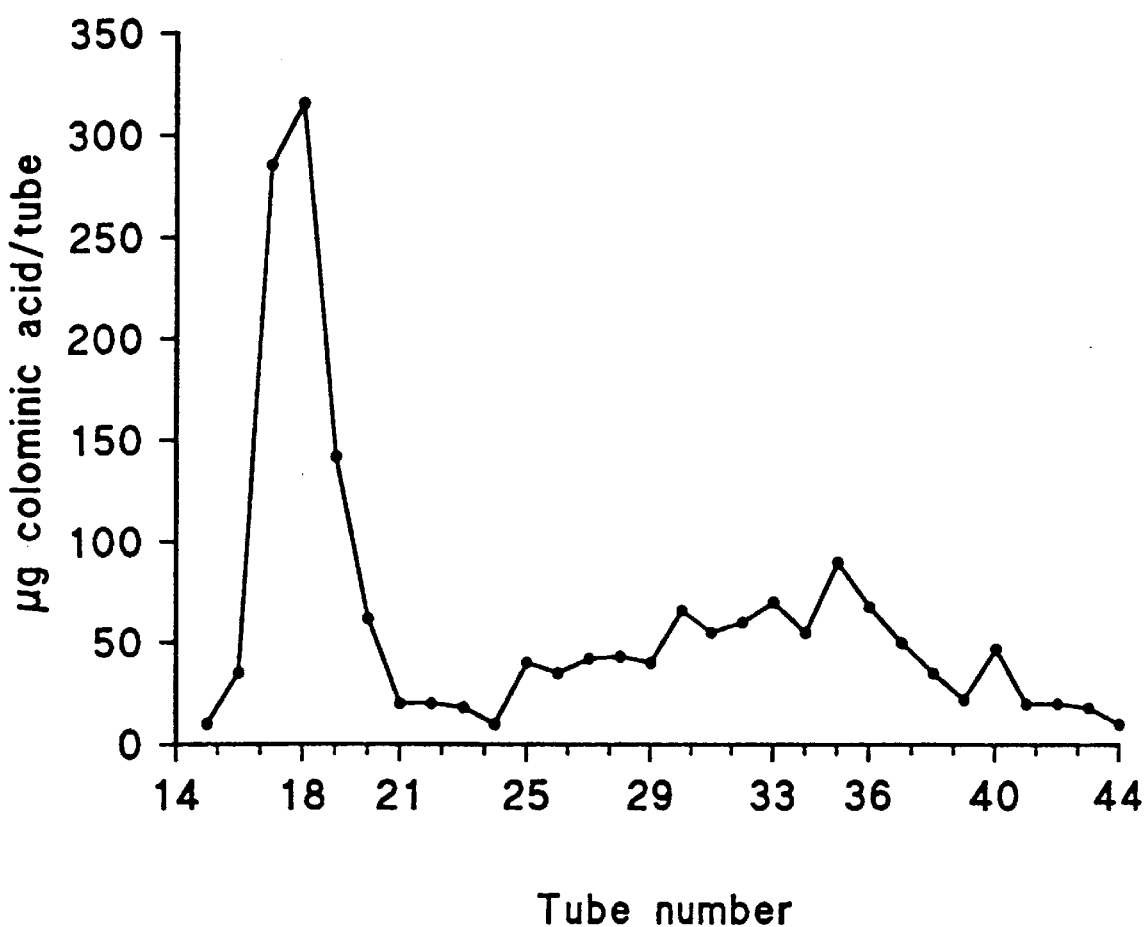
FIG. 9 shows elution profiles of liposomal $D_{11}$.

FIG. 7 shows the elution profiles of colominic acid and SUV (mixed before application). Two distinct peaks representing liposomes (fractions 14–22) and colominic acid (fractions 22–44) can be seen. Nearly 95% of the applied colominic acid was detected in these fractions. SUV incorporating $D_6$ or $D_{11}$ (see Schemes 1 and 2) were applied onto Sephadex G-200 columns. FIG. 8 shows the elution profile of liposomal $D_6$. About 51% of the colonminic acid derivative (D6) was recovered with liposomes (i.e. incorporated into the bilayers). A similar proportion (52.14%) of the colominic acid derivative $D_{11}$ (FIG. 9) was incorporated in SUV.

Example 8
Incorporation of polysaccharide B into liposomes

Experiments were carried out to ascertain whether polysaccharide B (PSB) could insert its phospholipid moiety into the bilayer of small unilamellar liposomes (SUV), render the liposomal surface hydrophilic and thus extend the half-life of the vesicles in the blood circulation.

Methodology

Egg phosphatidylcholine (PC) or distearoyl phosphatidylcholine (DSPC) and equimolar cholesterol (25 mg phospholipid and 12.5 mg cholesterol) were dissolved in chloroform. After the solvent was removed by rotary evaporation, 2 ml of 0.06M carboxyfluorescein (CF) also containing 1.2 mg polysaccharide B were added. The container was shaken vigorously to disrupt the lipid film and the suspension was bath sonicated for 3 min at 4° C. (PC) and 60° C. (DSPC SUV). The suspension was then probe sonicated at the same temperatures for 6 min with 30 seconds rest after each minute. The clear suspension containing the SUV was then passed through a Sepharose CL-4B column to separate liposome-incorporated CF and PSB from free materials. The pattern of separation from a typical experiment shows that 19.2% of PSB was recovered with the SUV fraction. Results of PSB incorporation in PC or DSPC SUV from eight experiments are shown in Table 7.

TABLE 7

Incorporation of PSB in SUV

| Experiment | Lipids used | PBS used (μg) | % PSB on SUV | μg PSB on SUV |
|---|---|---|---|---|
| 9.1 | PC,CHOL | 1200 | 19.2 | 236 |
| 9.2 | PC,CHOL | 1800 | 18.5 | 323 |
| 9.3 | PC,CHOL | 1400 | 19.9 | 278 |
| 9.4 | PC,CHOL | 1500 | 21.2 | 318 |
| 9.5 | PC,CHOL | 500 | 18.8 | 94 |
| 9.6 | PC,CHOL | 1500 | 22.2 | 333 |
| 9.7 | DSPC,CHOL | 500 | 29.0 | 145 |
| 9.8 | DSPC,CHOL | 1500 | 21.4 | 321 |

Example 10
The effect of PSB in SUV on vesicle clearance from the circulation of mice after I.V. injection T.O. mice were divided into two groups of two and injected into the tail vein with SUV composed of PC and cholesterol (molar ratio 1:1) and containing CF with or without incorporated PSB. They were injected intravenously with CF-containing SUV or with CF-containing SUV coated with 118 μg PSB. Animals were bled at time intervals after injection and blood plasma samples for total CF by the method of Kirby, Clarke and Gregoriadis (Biochem. Journal 186, 591 (1980)). Values are from individual animals and denote % of the injected liposomal CF per total blood.

Figure 10:
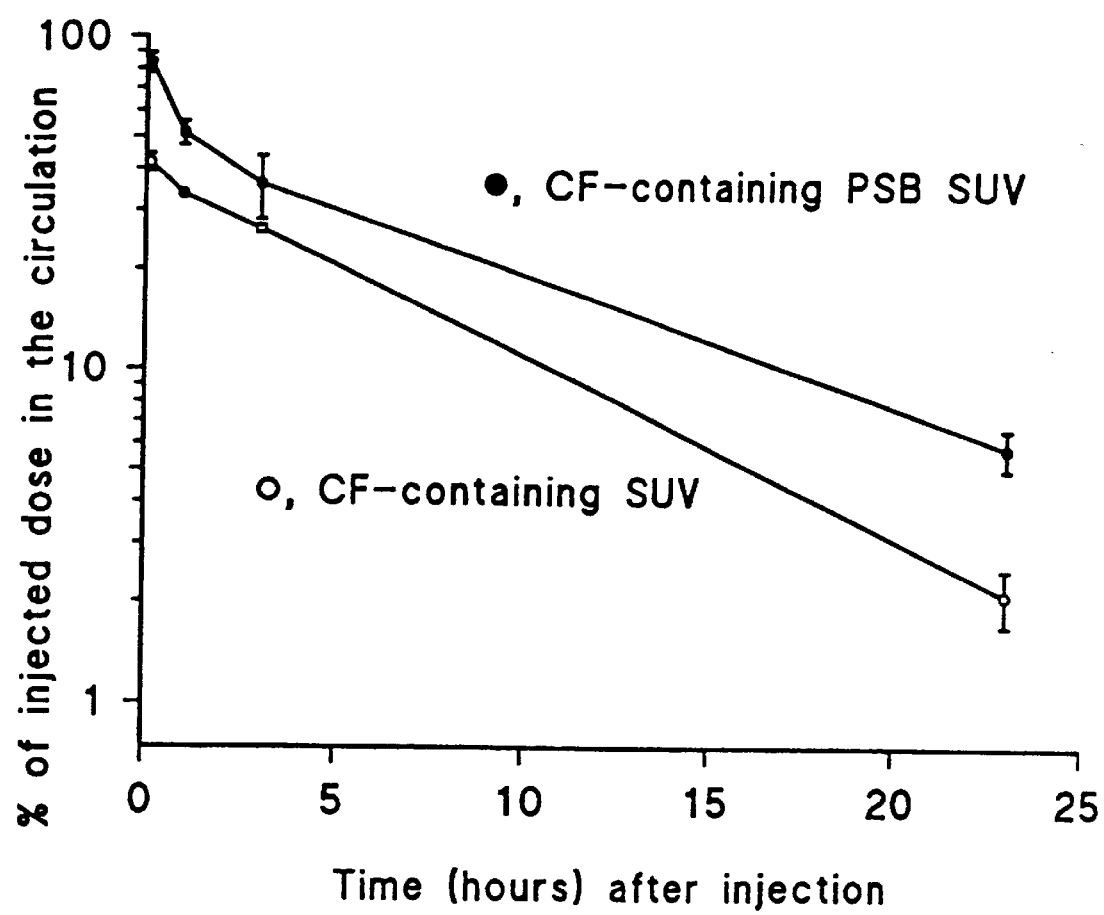
FIG. 10 shows the concentration of liposomal CF at time intervals after infection.
Figure 11:
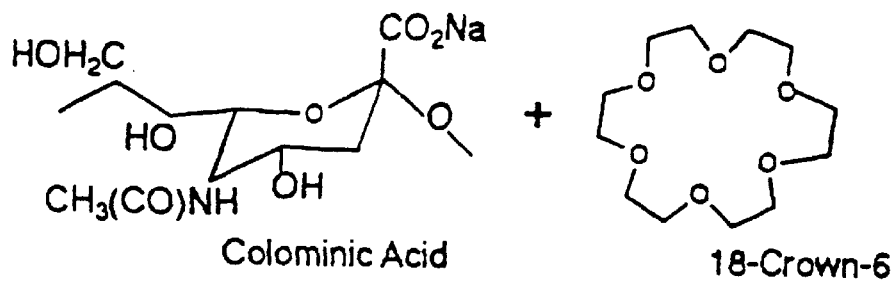
FIG. 11 shows coupling of 1-bromooctadecane with colominic acid.
Figure 11:
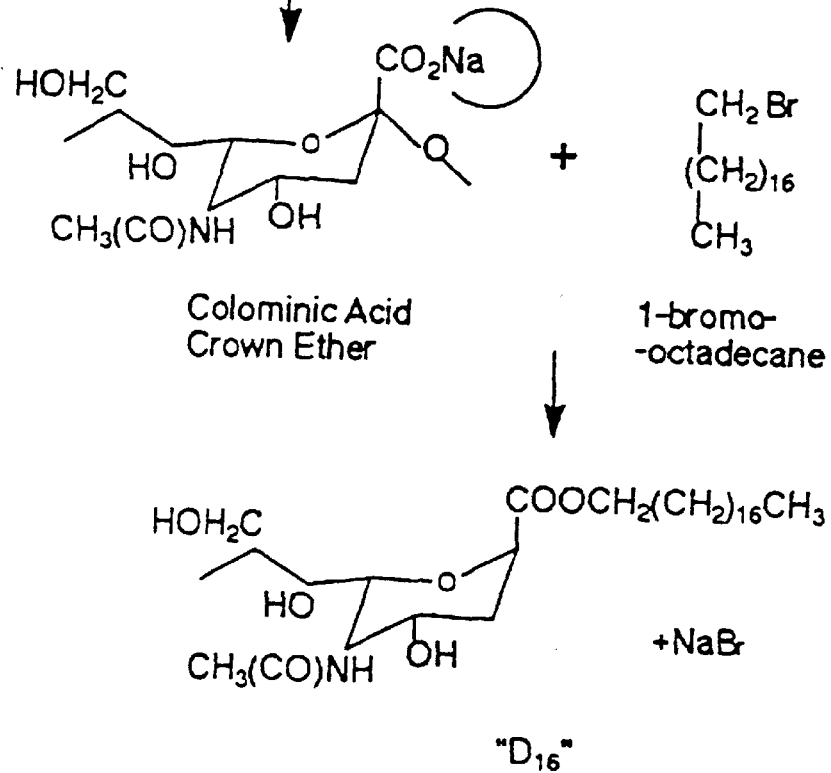

Results in Table 8 and FIG. 10 show the concentration of liposomal CF in their blood at time intervals after infection. Comparison of values from the two groups shows that the presence of PSB on the liposomal surface leads to a slower rate of clearance. Similar results were obtained in one other experiment with PSB-coated SUV made of DSPC and cholesterol as above and in one experiment with PSB-coated SUV made of DSPC and cholesterol.

TABLE 8

Clearance of Liposome-entrapped CF after IV injection

| Injected preparation | % of injected dose in total blood | | | |
|---|---|---|---|---|
| | 7 min | 1 h | 3 h | 23 h |
| CF-containing SUV | 44.3 | 33.9 | 25.7 | 2.5 |
| | 39.3 | 33.4 | 27.0 | 1.7 |
| PSB-coated CF-containing SUV | 89.1 | 47.1 | 28.2 | 5.0 |
| | 78.2 | 55.5 | 43.7 | 6.6 |

I claim:

1. A pharmaceutical compositon comprising a pharmaceutically active ingredient associated with a polysaccharide compound in an amount sufficient to extend the availability of the pharmaceutically active ingredient in the circulation of a patient, the polysaccharide compound consisting essentially of a chain of sialic acid units having at least 5 sialic acid units.

2. The pharmaceutical composition according to claim 1 in which the active ingredient and the polysaccharide compound are directly associated with each other.

3. The pharmaceutical composition according to claim 1 in which the active ingredient and the polysaccharide compound are associated with each other through the medium of a drug delivery system.

4. The pharmaceutical composition according to claim 3 in which the polysaccharide compound is associated with the drug delivery system by a covalent or non-covalent bond.

5. The pharmaceutical composition according to claim 3 in which the polysaccharide compound is bound to the surface of a liposome.

6. The pharmaceutical composition according to claim 3 containing a macromolecular DDS comprising of a peptide or protein component which is covalently bound to the polysaccharide compound.

7. The pharmaceutical composition according to claim 1 in which the polysaccharide compound is one in which the half-life of the polysaccharide compound in the circulation, following any initial rapid removal step, is at least 10 hours.

8. The pharmaceutical composition according to claim 1 in which the polysaccharide compound is a bacterial polysaccharide or derivative thereof.

9. The pharmaceutical composition according to claim 1 in which the polysaccharide compound has at least 20 sialic acid residues per molecule in the polysaccharide component.

10. The pharmaceutical composition according to claim 1 in which the polysaccharide is substantially free of terminal galactose, fucose and mannose units.

11. The pharmaceutical composition according to claim 10 in which the polysaccharide compound is selected from the group consisting of group B polysaccharides of *N. meningitidis, E. coli* K1, moraxella nonliquifaciens, and *Pasteurella aeroginosis*; group C of *N. meningitidis, E. coli* K92 polysaccharide; and colominic acid.

12. The pharmaceutical composition according to claim 1 in which the polysaccharide compound is the derivative of a glycolipid which has been subjected to alkaline hydrolysis to remove the fatty acid chains.

13. The pharmaceutical composition according to claim 1 in which the active ingredient comprises a peptide or a protein.

14. The pharmaceutical composition according to claim 9 in which the polysaccharide compound has at least 50 sialic acid units.

15. A liposome having bound to its external surface a moiety which consists essentially of a chain of sialic acid units having at least 5 sialic acid units.

16. The liposome according claim 15 in which the moiety is part of a polysaccharide compound which contains a hydrophobic portion which is incorporated into the lipid layer of the liposomes.

17. The liposome according claim 16 in which the polysaccharide compound is a naturally occurring glycolipid or a derivative thereof.

18. The liposome according claim 16 in which the polysaccharide compound has been derivatized with a hydrophobic portion.

19. A liposome according to claim 15 in which the polysaccharide compound has at least 20 sialic acid units and is substantially free of terminal galactose, fucose and mannose units and is selected from the group consisiting of B polysaccharides of *N. meningitidis, E. coli* K1*, moraxella nonliquifaciens, Pasteurella aeroginosis*; group C of *N. meningitidis, E. coli* K92 polysaccharide; and colominic acid.

20. The liposome according to claim 15 in combination with a pharmaceutically acceptable excipient.

21. The liposomes according to claim 20 in which the polysaccharide compound has at least 20 sialic acid units and is substantially free of terminal galactose, fucose and mannose units and is selected from the group consisiting of B polysaccharides of *N. meningitidis, E. coli* K1*, Moraxella nonliquifaciens, Pasteurella aeroginosis*; group C of *N. meningitidis, E. coli* K92 polysaccharide; and colominic acid.

22. The liposome according to claim 18 in which the hydrophobic portion is covalently bound to a sialic acid unit of the polysaccharide moiety.

23. The liposome according to claim 22 in which the hydrophobic portion is covalently bound to a sialic acid unit through the 1-position or the nitrogen atom.

24. In a method of producing liposomes from a mixture of liposome-forming lipids, the improvement which comprises of the inclusion of a polysaccharide compound which contains a subunit containing a chain of at least 5 sialic acid units and a hydrophobic portion.

25. The method according to claim 24 in which the polysaccharide compound is a naturally occurring glycolipid or a derivative thereof.

26. The method according to claim 24 in which the polysaccharide compound comprises a derivative of a naturally occurring polysaccharide to which a hydrophobic portion has been bound.

27. The method according to claim 26 in which the polysaccharide compound comprises a hydrophobic group joined by covalent linkage at the 1-position of a sialic acid residue.

28. The method according to claim 24 in which the polysaccharide compound has at least 20 sialic acid units and is substantially free of terminal galactose, fucose and mannose units and is selected from the group consisiting of B polysaccharides of *N. meningitidis, E. coli* K1, *Moraxella nonliquifaciens, Pasteurella aeroginosis*; group C of *N. meningitidis, E. coli* K92 polysaccharide; and colominic acid.

29. In a method of prolonging the availability of a pharmaceutically active ingredient in the circulation of a patient by combining the pharmaceutically active ingredient with an effective amount of a prolonging agent, the improvement which comprises of employing as the prolonging agent a polysaccharide compound consisting essentially of a chain of sialic acid and having at least 5 sialic acid units.

30. The method according to claim 29 in which the active ingredient and the polysaccharide compound are directly associated with each other.

31. A method according to claim 29 in which the active ingredient and the polysaccharide compound are associated with each other through the medium of a drug delivery system.

32. A method according to claim 31 in which the polysaccharide compound is bound to the surface of a liposome.

33. The method according to claim 31 in which the drug delivery system is a macromolecular DDS comprising of a peptide or protein component which is covalently bound to the polysaccharide compound.

34. The method according to claim 29 in which the polysaccharide compound is substantially free of terminal galactose, fucose and mannose units.

35. The method according to claim 34 in which the polysaccharide compound is the derivative of a glycolipid which has been subjected to alkaline hydrolysis to remove the fatty acid chains.

36. The method according to claim 29 in which the pharmaceutically active ingredient comprises a peptide or a protein.

37. The method according to claim 29 in which the polysaccharide compound has at least 50 sialic acid units.

* * * * *

UNITED STATES PATENT AND TRADEMARK OFFICE
CERTIFICATE OF CORRECTION

PATENT NO. : 5,846,951
DATED : December 8, 1998
INVENTOR(S) : Gregory Gregoriadis It is certified that error appears in the above-identified patent and that said Letters Patent is hereby corrected as shown below:

On the title page, Related U.S. Application Data, item [62] should read --Jun. 8, 1992 [WO] WIPO.........PCT/GB92/22331--.

Signed and Sealed this

Twenty-first Day of September, 1999

Attest:

Q. TODD DICKINSON

*Attesting Officer*   *Acting Commissioner of Patents and Trademarks*